US010287583B2

(12) United States Patent
Mamet et al.

(10) Patent No.: US 10,287,583 B2
(45) Date of Patent: May 14, 2019

(54) OLIGONUCLEOTIDE DECOYS FOR THE TREATMENT OF PAIN

(71) Applicant: Adynxx, Inc., San Francisco, CA (US)

(72) Inventors: Julien Mamet, San Francisco, CA (US); Rick Orr, San Francisco, CA (US); Don Manning, Bloomsbury, NJ (US); Scott Harris, San Francisco, CA (US); William Martin, Kensington, CA (US)

(73) Assignee: Adynxx, Inc., San Francisco, CA (US)

( * ) Notice: Subject to any disclaimer, the term of this patent is extended or adjusted under 35 U.S.C. 154(b) by 0 days.

(21) Appl. No.: 15/504,191

(22) PCT Filed: Aug. 14, 2015

(86) PCT No.: PCT/US2015/045268
§ 371 (c)(1),
(2) Date: Feb. 15, 2017

(87) PCT Pub. No.: WO2016/025829
PCT Pub. Date: Feb. 18, 2016

(65) Prior Publication Data
US 2017/0247694 A1 Aug. 31, 2017

Related U.S. Application Data

(60) Provisional application No. 62/037,996, filed on Aug. 15, 2014.

(51) Int. Cl.
*A61K 48/00* (2006.01)
*C07H 21/02* (2006.01)
*C07H 21/04* (2006.01)
*C12N 15/113* (2010.01)
*A61K 31/7088* (2006.01)
*A61K 45/06* (2006.01)

(52) U.S. Cl.
CPC ........ *C12N 15/113* (2013.01); *A61K 31/7088* (2013.01); *A61K 45/06* (2013.01); *C12N 2310/13* (2013.01)

(58) Field of Classification Search
CPC . C12N 15/113; C12N 2310/13; A61K 31/713
See application file for complete search history.

(56) References Cited

U.S. PATENT DOCUMENTS

| | | |
|---|---|---|
| 5,206,152 A | 4/1993 | Sukhatme |
| 5,504,075 A | 4/1996 | Burrows et al. |
| 5,683,985 A | 11/1997 | Chu et al. |
| 5,770,413 A | 6/1998 | Van Ooijen et al. |
| 6,004,813 A | 12/1999 | Serlupi-Crescenzi et al. |
| 6,008,048 A | 12/1999 | Monia et al. |
| 6,011,143 A | 1/2000 | Shionoya et al. |
| 6,022,863 A | 2/2000 | Peyman |
| 6,034,234 A | 3/2000 | Matsuo |
| 6,060,310 A | 5/2000 | Cho-Chung |
| 6,140,128 A | 10/2000 | Cohen et al. |
| 6,262,033 B1 | 7/2001 | Morishita et al. |
| 6,270,761 B1 | 8/2001 | Russell et al. |
| 6,316,190 B1 | 11/2001 | Rein et al. |
| 6,333,408 B1 | 12/2001 | Motojima et al. |
| 6,395,029 B1 | 5/2002 | Levy |
| 6,410,516 B1 | 6/2002 | Baltimore et al. |
| 6,410,721 B1 | 6/2002 | Hunt et al. |
| 6,432,641 B1 | 8/2002 | Lee et al. |
| 6,555,525 B2 | 4/2003 | Burke |
| 6,599,741 B1 | 7/2003 | Hecker et al. |
| 6,774,118 B1 | 8/2004 | Dzau et al. |
| 6,818,626 B1 | 11/2004 | Wolff et al. |
| 6,821,956 B2 | 11/2004 | Dzau et al. |
| 6,867,289 B1 | 3/2005 | Gorenstein et al. |
| 6,890,909 B1 | 5/2005 | Ono et al. |
| 6,927,027 B2 | 8/2005 | Erikson et al. |
| 6,969,704 B1 | 11/2005 | Pinsky et al. |
| 7,014,861 B2 | 3/2006 | Roorda et al. |
| 7,060,690 B2 | 6/2006 | Klem |
| 7,108,844 B2 | 9/2006 | Carpentier |
| 7,160,869 B2 | 1/2007 | Lee et al. |
| 7,186,556 B2 | 3/2007 | Hecker et al. |
| 7,256,182 B2 | 8/2007 | Lawrence, III et al. |
| 7,320,964 B2 | 1/2008 | Hecker et al. |
| 7,482,158 B2 | 1/2009 | Mathison |
| 7,524,949 B2 | 4/2009 | Hecker et al. |
| 7,585,848 B2 | 9/2009 | Masuda et al. |

(Continued)

FOREIGN PATENT DOCUMENTS

| | | |
|---|---|---|
| AU | 2014201462 A1 | 4/2014 |
| CA | 2583576 | 4/2006 |
| EP | 0572287 A2 | 12/1993 |
| EP | 1281763 A2 | 2/2003 |
| EP | 1298141 A1 | 4/2003 |
| EP | 1357184 A2 | 10/2003 |
| EP | 1690544 A2 | 8/2006 |
| JP | 2005-336081 A | 12/2005 |
| JP | 2010-526541 A | 9/2013 |
| JP | 2013-536195 A | 9/2013 |
| KR | 2005-0016361 A | 2/2005 |

(Continued)

OTHER PUBLICATIONS

Ahn et al., "Inhibitory effects of novel AP-1 decoy oligodeoxynucleotides on vascular smooth muscle cell proliferation in vitro and neointimal formation in vivo", *Circ Res*, 90:1325-1332 (2002).

(Continued)

*Primary Examiner* — Amy H Bowman
(74) *Attorney, Agent, or Firm* — Cooley LLP

(57) ABSTRACT

Provided are therapeutic agents such as double-stranded nucleic acids, termed oligonucleotide decoys, pharmaceutical compositions comprising the same, and related methods of modulating nociceptive signaling, for instance, to prevent and/or treat pain.

19 Claims, 15 Drawing Sheets
Specification includes a Sequence Listing.

(56) References Cited

U.S. PATENT DOCUMENTS

| | | | |
|---|---|---|---|
| 7,777,014 | B2 | 8/2010 | Cattaruzza et al. |
| 7,943,591 | B2 | 5/2011 | Mamet |
| 8,093,225 | B2 | 1/2012 | Mamet |
| 8,741,864 | B2 | 6/2014 | Mamet |
| 8,808,747 | B2 | 8/2014 | Brown et al. |
| 9,290,762 | B2 | 3/2016 | Mamet |
| 9,700,624 | B2 | 7/2017 | Mamet et al. |
| 10,041,069 | B2 | 8/2018 | Mamet |
| 2002/0192184 | A1 | 12/2002 | Carpentier et al. |
| 2003/0166555 | A1 | 9/2003 | Alberini et al. |
| 2004/0048820 | A1 | 3/2004 | Hecker et al. |
| 2004/0192598 | A1 | 9/2004 | Kragie |
| 2004/0229833 | A1 | 11/2004 | Dzau et al. |
| 2005/0192238 | A1 | 9/2005 | Hecker et al. |
| 2006/0069055 | A1 | 3/2006 | Dajee et al. |
| 2006/0116344 | A1 | 6/2006 | Morishita et al. |
| 2006/0122134 | A1 | 6/2006 | Cattaruzza et al. |
| 2006/0153847 | A1 | 7/2006 | Masuda |
| 2006/0154886 | A1 | 7/2006 | Weihe et al. |
| 2006/0166916 | A1 | 7/2006 | Mathison |
| 2006/0189564 | A1 | 8/2006 | Burright et al. |
| 2006/0293264 | A1 | 12/2006 | Grandis et al. |
| 2008/0300209 | A1 | 12/2008 | Mamet |
| 2009/0221686 | A1* | 9/2009 | Hecker ........... C12N 15/113 514/44 R |
| 2010/0305492 | A1 | 12/2010 | Lad et al. |
| 2011/0166212 | A1 | 7/2011 | Mamet |
| 2012/0046348 | A1 | 2/2012 | Valliant et al. |
| 2012/0225084 | A1* | 9/2012 | Goldberg ......... C07K 14/4702 424/172.1 |
| 2012/0232131 | A1 | 9/2012 | Mamet |
| 2013/0309201 | A1 | 11/2013 | Bazinet et al. |
| 2014/0221490 | A1 | 8/2014 | Lacouture et al. |
| 2014/0343132 | A1 | 11/2014 | Mamet |
| 2015/0111956 | A1 | 4/2015 | Mamet et al. |
| 2016/0222382 | A1 | 8/2016 | Mamet |
| 2018/0015165 | A1 | 1/2018 | Mamet et al. |

FOREIGN PATENT DOCUMENTS

| | | |
|---|---|---|
| WO | WO 1996/029433 A1 | 9/1996 |
| WO | WO 1999/026634 A1 | 6/1999 |
| WO | WO 2002/029044 A2 | 4/2002 |
| WO | WO 2002/041922 A1 | 5/2002 |
| WO | WO 2002/066071 A2 | 8/2002 |
| WO | WO 2002/070668 A2 | 9/2002 |
| WO | WO 2003/063799 A2 | 8/2003 |
| WO | WO 2003/091432 A1 | 11/2003 |
| WO | WO 2004/052401 A2 | 6/2004 |
| WO | WO 2005/004702 A2 | 1/2005 |
| WO | WO 2005/027830 A2 | 3/2005 |
| WO | WO 2006/035434 A2 | 4/2006 |
| WO | WO 2006/043722 A1 | 4/2006 |
| WO | WO 2006/086105 A2 | 8/2006 |
| WO | WO 2006/096498 A2 | 9/2006 |
| WO | WO 2008/141308 A2 | 11/2008 |
| WO | WO 2012/021985 A1 | 2/2012 |
| WO | WO 2012/177906 A1 | 12/2012 |
| WO | WO 2013/170086 A2 | 11/2013 |
| WO | WO 2016/025829 A1 | 2/2016 |
| WO | WO 2017/151644 A1 | 9/2017 |

OTHER PUBLICATIONS

Altschul et al., "Blast Help Manual", Nall. Cent. Biotechnol. Inf., Nall. Library Medicine, 9 pages. [downloaded May 5, 2015] http://dir.nhlbi.nih.gov/papers/Ikem/imcd/docs/Help.asp?blast_help.html.
Altschul et al., "Gapped BLAST and PSI-BLAST: a new generation of protein database search programs", Nucelic Acid Research, 1997, pp. 3389-3402, vol. 25, No. 17.
Australian Application No. 2008251320, Examination Report dated Sep. 4, 2012, 4 pages.
Australian Application No. 2014201462, Examination Report dated Sep. 4, 2015, 4 pages.
Australian Application No. 2014201462, Examination Report dated Jun. 30, 2016, 3 pages.
Borner et al., STAT6 transcription factor binding sites with mismatches within the canonicai 5'-TTC . . . GAA-3' motif involved in regulation of delta- and mu-opioid receptors, *J Neurochem*, 91[6]:1493-1500 (2004).
Buchwald et al., "Decoy oligodeoxynucleotide against activator protein-1 reduces neointimal proliferation after coronary angioplasty in hypercholesterolemic minipigs", *JACC*, 39:732-738 (2002).
Canadian Application No. 2,723,672, Office Action dated Nov. 30, 2015, 4 pages.
Cattaruzza et al., "Mechanosensitive transcription factors involved in endothelin B receptor expression", *J Bioi Chem*, 276[40]:36999-37003 (2001).
Chen et al., "Up-regulation of Egr1 by 1.25-dihydroxyvitamin D3 contributes to increased expression of p35 activator of cyclin-dependent kinase 5 and consequent onset of the terminal phase of HL60 cell differentiation", *Cancer Res*, 64[15]:5425-5433 (2004).
Cho et al., "A genomic-scale view of the cAMP response element-enhancer decoy: a tumor target based genetic tool", *PNAS*, 99[24]:15626-15631 (2002).
Cho et al., "Potentiation of lipopolysaccharide-inducible cyclooxygenase 2 expression by C2-ceramide via c-Jun N-terminal kinase-mediated activation of CCAAT/enhancer binding protein in macrophages", *Mol Pharmacol*, 63[3]:512-523 (2003).
D'Acquisto et al., "Local administration of transcription factor decoy oligonucleotides to nuclear factor-kB prevents carrageenin-induced inflammation in rat hind paw", *Gene Ther*, 7[20]:1731-1737 (2000).
Daftary, Gaurang S., et al. "A novel role of the Sp/KLF transcription factor KLF11 in arresting progression of endometriosis." PloS One (2013); 8.3: e60165.
Dash et al., "Sequestration of serum response factor in the hippocampus impairs long-term spatial memory", *J Neuroch*, 93:269-278 (2005).
Database EMBL [Online] Jul. 14, 2005 (Jul. 14, 2005), "EST1078622 Normalized pine embryo library, Lib_D Pinus taeda cDNA clone PWAC753 3-end, mRNA sequence.", XP002769924, retrieved from EBI Accession nN. EM_EST:DR688537 Database accession No. DR688537, 2 pages.
Dobi, A., and Agoston, D. V. "Submillimolar levels of calcium regulates DNA structure at the dinucleotide repeat (TG/AC) n." Proceedings of the National Academy of Sciences (1998); 95.11: 5981-5986.
Engleman and Marsala, "Efficacy of adding clonidine to intrathecal morphine in acute postoperative pain: meta-analysis." Br J Anaesth. (2013); 110(1): 21-27. Epub Sep. 21, 2012.
Enomoto, Takashi, et al. "Transcriptional regulation of an insulin-sensitizing adipokine adipolin/CTRP12 in adipocytes by Krüppel-like factor 15." PloS One (2013); 8.12: e83183.
Dzau, Victor J., "Transcription Factor Decoy," Circulation Research, 2002, vol. 90, pp. 1234-1236.
European Application No. 08755344.2, Extended European Search Report dated Oct. 12, 2011, 9 pages.
European Application No. 14179247.3, Supplementary European Search Report dated Dec. 3, 2014, 7 pages.
European Search Report, European Patent Application No. 13787024.2, dated Dec. 8, 2015, 9 pages.
European Search Report, European Patent Application No. 13787024.2, dated Apr. 13, 2017, 8 pages.
European Application No. EP 16199871.1, Extended European Search Report dated May 19, 2017, 9 pages.
Foti et al., "A nucleoprotein complex containing Sp1, C/EBPbeta, and HMGI-Y controls human insulin receptor gene transcription", *Mol Cell Biol*, 23[8]:2720-2732 (2003).
Gao et al., "A single decoy oligodeoxynucleotides targeting multiple oncoproteins produces strong anticancer effects", *Mol Pharmacal*, 70[5]:1621-1629 (2006).
Grote et al., "Stech-inducible expession of the angogenic facor CCN1 in vasular smooth muscle cells is mediated by Egr-1", *J Biol Chem.*, 279[53]:55675-555681 (2004).

(56) References Cited

OTHER PUBLICATIONS

Gupta and Kone, "USF-1 and USF-2 trans-repress IL-1beta-induced iNOS transcription in mesangial cells", *Am J Physical Cell Physiol*, 283:C1065-1072 (2002).
Hasan and MacDonald, "Sp/Kruppel-like transcription factors are essential for the expression of mitochondrial glycerol phosphate dehydrogenase promoter B," Gene, 296(1-2):221-234 (2002).
Herdegen and Leah, "Inducible and constitutive transcription factors in the mammalian nervous system: control of gene expression by Jun, Fos and Krox, and CREB/ATF proteins", *Brain Res Brain Res Rev.*, 28[3]:370-490 (1998).
Igwe, O.J., "Modulation of peripheral inflammation in sensory ganglia by nuclear factor kB decoy oligodeoxynucleotide: involvement of SRC kinase pathway", *Neurosci Lett.*, 381[1-2]:114-119 (2005).
Ishibashi et al., "Sp1 decoy transfected to carcinoma cells suppresses the expression of vascular endothelial growth factor, transforming growth factor b1, and tissue factor and also cell growth and invasion activities", *Cancer Res.*, 60:6531-6536 (2000).
International Search Report and Written Opinion, International Application No. PCT/US2008/063471, dated Jan. 14, 2009, 9 pages.
International Preliminary Report on Patentability, International Application No. PCT/US2008/063471, dated Nov. 17, 2009, 6 pages.
International Preliminary Report on Patentability for PCT Application No. PCT/US2013/040426 dated Nov. 11, 2014 (7 pages).
Written Opinion for PCT Application No. PCT/US2013/040426 dated Nov. 26, 2013 (6 pages).
International Search Report for PCT Application No. PCT/US2013/040426 dated Jan. 20, 2014 (5 pages).
International Search Report and Written Opinion, International Application No. PCT/US2015/045268, dated Oct. 28, 2015, 16 pages.
International Preliminary Report on Patentability, International Application No. PCT/US2015/045268, dated Feb. 21, 2017, 12 pages.
International Search Report and Written Opinion, International Application No. PCT/US2017/019989, dated Jul. 19, 2017, 23 pages.
Japanese Application No. 2010-507728, Office Action dated Feb. 1, 2013 (English translation), 10 pages.
Kajimura, D., et al., "Identification of genes regulated by transcription factor KLF7 in differentiating olfactory sensory neurons." Gene (2007); 388(1-2): 34-42.
Kamimura et al., "Platelet-derived growth factor induces tissue factor expression in vascular smooth muscle cells via activation of Egr-1", *Hypertension*, 44[6]:944-951 (2004).
Kelkenberg et al., "CCAAT/enhancer-binding protein decoy oligodeoxynucleotide inhibition of macrophage-rich vascular lesion formation in hypercholesterolemic rabbits", *Arterioscler Thromb Vase Biol.*, 22:949-954 (2004).
Ko, S.W. et al., "Selective Contribution of Egr1 (Zif/268) to Persistent Inflammatory Pain", *Journal of Pain*, 6[1]:12-20 (2005).
Kohlstedt, K. et al., "Signaling via the angiotensin-converting enzyme enhances the expression of cyclooxygenase-2 in endothelial cells", *Hypertension*, 45:126-132 (2005).
Kraus et al., "The role of nuclear factor kappaB in tumor necrosis factor-regulated transcription of the human mu-opioid receptor gene", *Mol Pharmacol*, 64[4]:876-884 (2003).
Lee et al., "Spinal NFKB activation induces COX2 upregulation and contributes to inflammatory pain hypersensitivity", *Eur J Neurosci*, 19:3375-3381 (2004).
Lei, Lei, et al. "The zinc finger transcription factor Klf7 is required for TrkA gene expression and development of nociceptive sensory neurons." Genes & development 19.11 (2005): 1354-1364.
Lei, L., et al., "mKlf7, a potential transcriptional regulator of TrkA nerve growth factor receptor expression in sensory and sympathetic neurons." Development (2001); 128(7): 1147-1158.
Leong et al., "Targeted inhibition of Stat3 with a decoy oligonucleotide abrogates head and neck cancer cell growth", *PNAS*, 100[7]:4138-4143 (2003).
Lesniak and Kuznicki, "Binding and functional characteristics of two E-box motifs within the S1OOA6 (calcyclin) gene promoter", *J Cell Biochem*, 97[5]:1017-1024 (2006).
Lim et al., "Sequence-independent inhibition of RNA transcription by DNA dumbbells and other decoys", *Nucl Acids Res.*, 25[3]:575-581 (1997).
Ma et al., "Intrathecal injection of cAMP response element binding protein (CREB) antisense oligonucloetide attenuates tactile allodynia caused by partial sciatic nerve ligation", *Brain Research*, 988:97-104 (2003).
Mamet, J., et al., "Single intrathecal administration of the transcription factor decoy AYX1 prevents acute and chronic pain after incisional, inflammatory, or neuropathic injury." Pain (2013); 155(2): 322-333.
Mann et al., "Ex-vivo gene therapy of human vascular bypass grafts with E2F decoy: the PREVENT single-centre randomised controlled trial", *The Lancet*, 354:1493-1498 (1999).
Matsumoto, Nobukyuki, et al. "Cloning the cDNA for a new human zinc finger protein defines a group of closely related Krüppel-like transcription factors." Journal of Biological Chemistry (1998); 273.43: 28229-28237.
Morishita et al., "A gene therapy strategy using a transcription factor decoy of the E2F binding site inhibits smooth muscle proliferation in vivo", *PNAS*, 92:5855-5859 (1995).
Motojima et al., "Sp1-like activity mediates angotensin-II-induced plasminogen-activator inhibitor type-1 (PAI-1) gene expression in mesangial cells", *Biochem J.*, 349:435-441 (2000).
Office Action, Japanese Application No. 201380036825.2, dated Jan. 15, 2016, 5 pages.
Ohtani et al., "Inhibition of neointimal hyperplasia after balloon injury by cis-element 'decoy' of early growth response gene-1 in hypercholesterolemic rabbits", *Gene Ther*, 11[2]:126-132 (2004).
Park et al., "Dual blockade of cyclic AMP response element— (CRE) and AP-1-directed transcription by CRE-transcription factor decoy oligonucleotide gene-specific inhibition of tumor growth", *J Biol Chem.*, 274[3]:1573-1580 (1999).
Rygh et al., "Local and descending circuits regulate long-term potentiation and zif268 expression in spinal neurons", *Eur J Neuroscience*, 24[3]:761-772 (2006).
Sahin et al., "Inactivation of Ets 1 transcription factor by a specific decoy strategy reduces rat C6 glioma cell proliferation and mmp-9 expression", *Int J Mol Med*, 15:771-776 (2005).
Sakaue, G. et al, "NF-kB decoy suppresses cytokine expression and thermal hyperalgesia in a rat neuropathic pain model", *NeuroReport*, 12[10]:2079-2084 (2001).
Sassa, Y. et al., "Functional role of Egr-1 mediating VEGF-induced tissue factor expression in the retinal capillary endothelium", *Graefes Arch Clin Exp Ophthalmol*, 240[12]:1003-1010 (2002).
Search Report, Japanese Application No. 201380036825.2, dated Jan. 7, 2016, 3 pages.
Shields, Janiel M., and Yang, Vincent W. "Identification of the DNA sequence that interacts with the gut-enriched Krüppel-like factor." Nucleic Acids Research (1998); 26.3: 796-802.
Steiger et al., "cAMP response element-binding protein, activating transcription factor-4, and upstream stimulatory factor differentially control hippocampal $GABA_BR1a$ and $GABA_BR1b$ subunit gene expression through alternative promoters", *J Neurosci*, 24[27]:6115-6126 (2004).
Sun, T. et al., "Alleviation of neuropathic pain by intrathecal injection of antisense oligonucleotides to p65 subunit of NF-kappa B", *British Journal of Anaesthesia*, 97(4):553-558 (2006).
Suzuki et al., "Initial clinical cases of the use of a NF-kB decoy at the site of coronary stenting for the prevention of restenosis", *Circ Journal*, 68:270-271 (2004).
Swirnoff and Milbrandt, "DNA-Binding Specificity of NGFI-A and Related Zinc Finger Transcription Factors", *Molecular and Cellular Biology*, 15[4]:2275-2287 (1995).
Szpara, M.L., et al., "Analysis of gene expression during neurite outgrowth and regeneration." BMC Neurosci. (2007); 8: 100, 17 pages.

(56) References Cited

OTHER PUBLICATIONS

Taimor et al., "Transcription activator protein 1 (AP-1) mediates alpha- but not beta-adrenergic hypertrophic growth responses in adult cardiomyocytes", *Am J Physiol Heart Circ Physiol*, 286[6]:H2369-H2375 (2004).

Tanaka et al., "Sequence-specific interaction of alpha-beta-anomeric double stranded DNA with the p50 subunit of NFKB: application to the decoy approach", *Nucl Acids Res*, 22[15]:3069-3074 (1994).

Todorovic, et al., "T-type voltage-gated calcium channels as targets for the development of novel pain therapies." Br J Pharmacol. (2011); 163(3): 484-495.

Uchida et al., "Ceramide reduction and transcriptional up-regulation of glucosylceramide synthase through doxorubicin-activated Sp1 in drug-resistant HL-60/ADR cells", *Cancer Res*, 64:6271-6279 (2004).

Van Vliet, J., et al., "Human KLF17 is a new member of the Sp/KLF family of transcription factors." Genomics (2006); 87(4): 474-482.

Verrecchia et al., "Blocking Sp1 transcription factor broadly inhibits extracellular matrix gene expression in vitro and in vivo: implications for the treatment of tissue fibrosis", *J Invest Dermatol*, 116[5]:755-763 (2001).

Viedt et al., "The terminal complement complex C5b-9 stimulates interleukin-6 production in human smooth muscle cells through activation of transcription factors NF-kB and AP-1", *FASEB J*, 14:2370-2372 (2000).

Wagner et al., "Decoy Oligodeoxoynucleotide characterization of transcription factors controlling endothelin-B receptor expression in vascular smooth muscle cells", *Mol Pharmacol*, 58[6]:1333-1340 (2000).

Wang et al., "Dose-related antiallodynic effects of cyclic AMP response element-binding protein-antisense oligonucleotide in the spared nerve injury model of neuropathic pain", *Neuroscience*,139[3]:1083-1093 (2006).

Xiang et al., "Egr-1 mediates SiO(2-driven transcription of membrane type I matrix metalloproteinase in macrophages", *J Huazhong Univ Sci Technolog Med Sci*, 27[1]:13-16 (2007).

Xu, Yisheng et al., "Multimerization and Aggregation of Native-State Insulin: Effect of Zinc," Langmuir, Jan. 10, J012, pp. 579-586, vol. 28, No. 1.

Yang et al., "Thrombospondin-1 mediates distal tubule hypertrophy induced by glycated albumin", *Biochem J*, 379:89-97 (2004).

Zanetti et al., "Inhibition of Sp1 activity by a decoy PNA-DNA chimera prevents urokinase receptor expression and migration of breast cancer cells", *Biochem Pharmacol.*, 70[9]:1277-1287 (2005).

Zhang, P. et al., "Egr-1 mediates hypoxia-inducible transcription of the NORG1 gene through an overlapping Egr-1/Sp1 binding site in the promoter", *Cancer Research*, 67(19):9125-9133 (2007).

European Application No. 15832083.8, Partial Supplementary European Search Report dated Nov. 29, 2017, 31 pages.

Kaushik, et al., "Therapeutic targeting of Krüppel-like factor 4 abrogates microglial activation." Journal of Neuroinflammation (2012); 9: 57.

European Application No. 15832083.8, Extended European Search Report dated Mar. 2, 2018, 26 pages.

Viktorov, A.L., "NSAIDs and pharmacotherapy of chronic pain: problems efficiency and safety." Rational Pharmacotherapy (2011); 1 (18): 37-46 [A.L. Viktorov, GU "NSC" academician N. D. Strazhesko Institute of Cardiology "AMS of Ukraine", SE "State Expert Center of the Ministry of Health of Ukraine", Kiev Continuance. Beginning at No. 4 (17) 2010], and English summary/translation of pertinent portions, 11 pages.

\* cited by examiner

FIG. 1

| Decoy | Binding level (OD450) | | | KLF15/KLF9 ratio | Neuropathic pain reduction |
|---|---|---|---|---|---|
| | KLF6 | KLF9 | KLF15 | | |
| TFDC1 | 0.07 | 0.15 | 0.21 | 1.39 | 55% |
| TFD16 | 0.38 | 0.26 | 0.38 | 1.46 | 49% |
| 16.6.5 | 0.14 | 0.20 | 0.30 | 1.52 | 44% |
| 16.6.2 | 0.32 | 0.32 | 0.45 | 1.39 | 43% |
| 17.5 | 0.30 | 0.29 | 0.35 | 1.23 | 37% |
| TFD17 | 0.27 | 0.21 | 0.29 | 1.42 | 32% |
| TFD3 | 0.21 | 0.18 | 0.09 | 0.49 | 24% |
| 17.1 | 0.16 | 0.37 | 0.17 | 0.46 | 20% |
| 17.9 | 0.35 | 0.24 | 0.21 | 0.89 | 1% |
| 16.9 | 0.26 | 0.31 | 0.28 | 0.89 | 0% |
| TFDC2 | 0.13 | 0.21 | 0.18 | 0.86 | -10% |

*FIG. 4A*

| Parameter | Linear Correlation Coefficient | Linear Correlation Coefficient (ratio ~ 0.9 excluded) |
|---|---|---|
| KLF15/KLF9 | 0.5 | 0.7 |
| 1/(KLF15/KLF9) | 0.2 | 0.7 |
| 1/(KLF15/KLF6/KLF9) | 0.2 | 0.6 |
| KLF15/KLF6/KLF9 | 0.2 | 0.5 |
| KLF6/KLF15 | 0.1 | 0.4 |
| 1/(KLF15/KLF6) | 0.1 | 0.4 |
| 1/KLF15 | 0.1 | 0.3 |
| KLF15 | 0.2 | 0.3 |
| 1/(KLF6+KLF9) | 0.1 | 0.2 |
| KLF9 | 0.0 | 0.1 |
| 1/KLF6 | 0.1 | 0.1 |
| 1/KLF9 | 0.1 | 0.1 |
| KLF6+KLF15 | 0.0 | 0.1 |
| 1/(KLF6+KLF15) | 0.0 | 0.1 |
| 1/(KLF9+KLF15) | 0.0 | 0.1 |
| KLF9+KLF15 | 0.1 | 0.0 |
| KLF6+KLF9 | 0.0 | 0.0 |
| KLF6+KLF9+KLF15 | 0.0 | 0.0 |
| 1/(KLF6/KLF9) | 0.0 | 0.0 |
| KLF6 | 0.0 | 0.0 |
| 1/(KLF6+KLF9+KLF15) | 0.0 | 0.0 |
| KLF6/KLF9 | 0.0 | 0.0 |

*FIG. 4B*

| Decoy | Binding level (OD450) | | | 1/(KLF6+KLF9) | Neuro-inflammatory pain reduction |
|---|---|---|---|---|---|
| | KLF6 | KLF9 | KLF15 | | |
| TFD17 | 0.27 | 0.21 | 0.30 | 2.09 | 33% |
| 16.6.2 | 0.32 | 0.32 | 0.45 | 1.56 | 30% |
| 17.5 | 0.30 | 0.29 | 0.35 | 1.72 | 29% |
| 17.1 | 0.16 | 0.37 | 0.17 | 1.90 | 28% |
| 16.6.5 | 0.14 | 0.20 | 0.30 | 2.93 | 22% |
| 16.9 | 0.26 | 0.31 | 0.28 | 1.76 | 21% |
| TFD16 | 0.38 | 0.26 | 0.38 | 1.55 | 18% |
| 17.9 | 0.35 | 0.24 | 0.21 | 1.70 | 15% |
| TFD3 | 0.21 | 0.18 | 0.09 | 2.59 | 14% |
| TFDC2 | 0.13 | 0.21 | 0.18 | 2.96 | 6% |
| TFDC1 | 0.07 | 0.15 | 0.21 | 4.52 | -3% |

FIG. 5A

| Parameter | Linear correlation coefficient ($R^2$) |
|---|---|
| 1/(KLF6+KLF9) | 0.6 |
| 1/(KLF6+KLF9+KLF15) | 0.6 |
| 1/KLF6 | 0.5 |
| 1/KLF9 | 0.5 |
| KLF6+KLF9 | 0.5 |
| KLF9+KLF15 | 0.5 |
| KLF6+KLF9+KLF15 | 0.5 |
| 1/(KLF6+KLF15) | 0.4 |
| KLF9 | 0.4 |
| 1/(KLF9+KLF15) | 0.4 |
| KLF15/KLF6/KLF9 | 0.4 |
| KLF6+KLF15 | 0.3 |
| KLF6 | 0.3 |
| KLF15 | 0.3 |
| 1/(KLF15/KLF6) | 0.2 |
| 1/KLF15 | 0.1 |
| 1/(KLF6/KLF9) | 0.1 |
| KLF6/KLF9 | 0.1 |
| 1/(KLF15/KLF6/KLF9) | 0.1 |
| KLF6/KLF15 | 0.0 |
| KLF15/KLF9 | 0.0 |
| 1/(KLF15/KLF9) | 0.0 |

*FIG. 5B*

SEQUENCE LISTING

```
<160> NUMBER OF SEQ ID NOS: 42

<210> SEQ ID NO 1
<211> LENGTH: 32
<212> TYPE: DNA
<213> ORGANISM: Artificial Sequence
<220> FEATURE:
<223> OTHER INFORMATION: KLF decoy oligonucleotide
<220> FEATURE:
<221> NAME/KEY: misc_feature
<222> LOCATION: (1)..(4)
<223> OTHER INFORMATION: nucleotides 1-4 may or may not be present
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (19)..(32)
<223> OTHER INFORMATION: nucleotides 19-32 may or may not be present

<400> SEQUENCE: 1
atccttygmm tyykycnhhn nvnnymhwbv aw                                    32

<210> SEQ ID NO 2
<211> LENGTH: 28
<212> TYPE: DNA
<213> ORGANISM: Artificial Sequence
<220> FEATURE:
<223> OTHER INFORMATION: KLF decoy oligonucleotide
<220> FEATURE:
<221> NAME/KEY: misc_feature
```

```
<222> LOCATION: (1)..(5)
<223> OTHER INFORMATION: nucleotides 1-5 may or may not be present
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(28)
<223> OTHER INFORMATION: nucleotides 19-28 may or may not be present

<400> SEQUENCE: 2
tgtkbkkddv dnsdnbnndv mbvmhrma                                      28

<210> SEQ ID NO 3
<211> LENGTH: 18
<212> TYPE: DNA
<213> ORGANISM: Artificial Sequence
<220> FEATURE:
<223> OTHER INFORMATION: KLF decoy oligonucleotide

<400> SEQUENCE: 3
tttgcctcct tcgatccc                                                 18

<210> SEQ ID NO 4
<211> LENGTH: 18
<212> TYPE: DNA
<213> ORGANISM: Artificial Sequence
<220> FEATURE:
<223> OTHER INFORMATION: KLF decoy oligonucleotide

<400> SEQUENCE: 4
atcctttgcc tccttcga                                                 18

<210> SEQ ID NO 5
<211> LENGTH: 32
<212> TYPE: DNA
<213> ORGANISM: Artificial Sequence
<220> FEATURE:
<223> OTHER INFORMATION: KLF decoy oligonucleotide

<400> SEQUENCE: 5
atcctttgcc tccttccctt tgcctccttc aa                                 32

<210> SEQ ID NO 6
<211> LENGTH: 28
<212> TYPE: DNA
<213> ORGANISM: Artificial Sequence
<220> FEATURE:
<223> OTHER INFORMATION: KLF decoy oligonucleotide

<400> SEQUENCE: 6
cctttgcctc cttcccttttg cctccttc                                     28

<210> SEQ ID NO 7
<211> LENGTH: 32
<212> TYPE: DNA
<213> ORGANISM: Artificial Sequence
<220> FEATURE:
<223> OTHER INFORMATION: KLF decoy oligonucleotide
```

```
<400> SEQUENCE: 7
atcctttgcc tccttcgaag gaggcaaagg at                    32

<210> SEQ ID NO 8
<211> LENGTH: 31
<212> TYPE: DNA
<213> ORGANISM: Artificial Sequence
<220> FEATURE:
<223> OTHER INFORMATION: KLF decoy oligonucleotide

<400> SEQUENCE: 8
atcctttgcc tccttccttt gcctccttca a                     31

<210> SEQ ID NO 9
<211> LENGTH: 27
<212> TYPE: DNA
<213> ORGANISM: Artificial Sequence
<220> FEATURE:
<223> OTHER INFORMATION: KLF decoy oligonucleotide

<400> SEQUENCE: 9
atcctttgcc tccttcgcct ccttcaa                          27

<210> SEQ ID NO 10
<211> LENGTH: 23
<212> TYPE: DNA
<213> ORGANISM: Artificial Sequence
<220> FEATURE:
<223> OTHER INFORMATION: KLF decoy oligonucleotide

<400> SEQUENCE: 10
cctttgcctc cttcgcctcc ttc                              23

<210> SEQ ID NO 11
<211> LENGTH: 24
<212> TYPE: DNA
<213> ORGANISM: Artificial Sequence
<220> FEATURE:
<223> OTHER INFORMATION: KLF decoy oligonucleotide

<400> SEQUENCE: 11
atcctttgcc tccttctcct tcaa                             24

<210> SEQ ID NO 12
<211> LENGTH: 24
<212> TYPE: DNA
<213> ORGANISM: Artificial Sequence
<220> FEATURE:
<223> OTHER INFORMATION: KLF decoy oligonucleotide

<400> SEQUENCE: 12
atcctttgcc tttgcctcct tcaa                             24

<210> SEQ ID NO 13
<211> LENGTH: 20
<212> TYPE: DNA
<213> ORGANISM: Artificial Sequence
<220> FEATURE:
<223> OTHER INFORMATION: KLF decoy oligonucleotide

<400> SEQUENCE: 13
cctttgcctt tgcctccttc                                  20

<210> SEQ ID NO 14
<211> LENGTH: 15
```

```
<212> TYPE: DNA
<213> ORGANISM: Artificial Sequence
<220> FEATURE:
<223> OTHER INFORMATION: KLF decoy oligonucleotide

<400> SEQUENCE: 14
tgtttgggag agctt                                                    15

<210> SEQ ID NO 15
<211> LENGTH: 15
<212> TYPE: DNA
<213> ORGANISM: Artificial Sequence
<220> FEATURE:
<223> OTHER INFORMATION: KLF decoy oligonucleotide

<400> SEQUENCE: 15
gctttgggag gatac                                                    15

<210> SEQ ID NO 16
<211> LENGTH: 16
<212> TYPE: DNA
<213> ORGANISM: Artificial Sequence
<220> FEATURE:
<223> OTHER INFORMATION: KLF decoy oligonucleotide

<400> SEQUENCE: 16
tgggagagct ttggga                                                   16

<210> SEQ ID NO 17
<211> LENGTH: 24
<212> TYPE: DNA
<213> ORGANISM: Artificial Sequence
<220> FEATURE:
<223> OTHER INFORMATION: KLF decoy oligonucleotide

<400> SEQUENCE: 17
tgtttgggag atttggagg atac                                           24

<210> SEQ ID NO 18
<211> LENGTH: 20
<212> TYPE: DNA
<213> ORGANISM: Artificial Sequence
<220> FEATURE:
<223> OTHER INFORMATION: KLF decoy oligonucleotide

<400> SEQUENCE: 18
tttgggagat ttgggaggat                                               20

<210> SEQ ID NO 19
<211> LENGTH: 24
<212> TYPE: DNA
<213> ORGANISM: Artificial Sequence
<220> FEATURE:
<223> OTHER INFORMATION: KLF decoy oligonucleotide

<400> SEQUENCE: 19
tgtttgggag aatcctccca aagc                                          24

<210> SEQ ID NO 20
<211> LENGTH: 20
<212> TYPE: DNA
<213> ORGANISM: Artificial Sequence
<220> FEATURE:
<223> OTHER INFORMATION: KLF decoy oligonucleotide

<400> SEQUENCE: 20
```
tttgggagaa tcctcccaaa                                                 20

<210> SEQ ID NO 21
<211> LENGTH: 27
<212> TYPE: DNA
<213> ORGANISM: Artificial Sequence
<220> FEATURE:
<223> OTHER INFORMATION: KLF decoy oligonucleotide

<400> SEQUENCE: 21
tgtttgggag agctatcctc ccaaagc                                         27

<210> SEQ ID NO 22
<211> LENGTH: 23
<212> TYPE: DNA
<213> ORGANISM: Artificial Sequence
<220> FEATURE:
<223> OTHER INFORMATION: KLF decoy oligonucleotide

<400> SEQUENCE: 22
tttgggagag ctatcctccc aaa                                             23

<210> SEQ ID NO 23
<211> LENGTH: 21
<212> TYPE: DNA
<213> ORGANISM: Artificial Sequence
<220> FEATURE:
<223> OTHER INFORMATION: KLF decoy oligonucleotide

<400> SEQUENCE: 23
tgtttgggag agggaggata c                                               21

<210> SEQ ID NO 24
<211> LENGTH: 21
<212> TYPE: DNA
<213> ORGANISM: Artificial Sequence
<220> FEATURE:
<223> OTHER INFORMATION: KLF decoy oligonucleotide

<400> SEQUENCE: 24
tgtttgggtt tgggaggata c                                               21

<210> SEQ ID NO 25
<211> LENGTH: 25
<212> TYPE: DNA
<213> ORGANISM: Artificial Sequence
<220> FEATURE:
<223> OTHER INFORMATION: KLF decoy oligonucleotide

<400> SEQUENCE: 25
cctttgcctc cttcgcctcc ttcaa                                           25

<210> SEQ ID NO 26
<211> LENGTH: 25
<212> TYPE: DNA
<213> ORGANISM: Artificial Sequence
<220> FEATURE:
<223> OTHER INFORMATION: KLF decoy oligonucleotide

<400> SEQUENCE: 26
tcctttgcct ccttcgcctc cttca                                           25

<210> SEQ ID NO 27
<211> LENGTH: 24
<212> TYPE: DNA
<213> ORGANISM: Artificial Sequence
<220> FEATURE:
<223> OTHER INFORMATION: KLF decoy oligonucleotide

<400> SEQUENCE: 27
cctttgcctc cttcgcctcc ttca                                           24

<210> SEQ ID NO 28
<211> LENGTH: 18
<212> TYPE: DNA
<213> ORGANISM: Artificial Sequence
<220> FEATURE:
<223> OTHER INFORMATION: KLF decoy oligonucleotide

<400> SEQUENCE: 28
atccttcgcc tccttcaa                                                  18

<210> SEQ ID NO 29
<211> LENGTH: 24
<212> TYPE: DNA
<213> ORGANISM: Artificial Sequence
<220> FEATURE:
<223> OTHER INFORMATION: KLF decoy oligonucleotide

<400> SEQUENCE: 29
atccttcgcc ttcgcctcct tcaa                                           24

<210> SEQ ID NO 30
<211> LENGTH: 27
<212> TYPE: DNA
<213> ORGANISM: Artificial Sequence
<220> FEATURE:
<223> OTHER INFORMATION: KLF decoy oligonucleotide

<400> SEQUENCE: 30
atccttcgcc tccttcgcct ccttcaa                                        27

<210> SEQ ID NO 31
<211> LENGTH: 22
<212> TYPE: DNA
<213> ORGANISM: Artificial Sequence
<220> FEATURE:
<223> OTHER INFORMATION: KLF decoy oligonucleotide

<400> SEQUENCE: 31
tgtttgggag aatcctccca aa                                             22

<210> SEQ ID NO 32
<211> LENGTH: 22
<212> TYPE: DNA
<213> ORGANISM: Artificial Sequence
<220> FEATURE:
<223> OTHER INFORMATION: KLF decoy oligonucleotide

<400> SEQUENCE: 32
tttgggagaa tcctcccaaa gc                                             22

<210> SEQ ID NO 33
<211> LENGTH: 22
<212> TYPE: DNA
<213> ORGANISM: Artificial Sequence
<220> FEATURE:
<223> OTHER INFORMATION: KLF decoy oligonucleotide

<400> SEQUENCE: 33
gtttgggaga atcctcccaa ag                                             22

```
<210> SEQ ID NO 34
<211> LENGTH: 25
<212> TYPE: DNA
<213> ORGANISM: Artificial Sequence
<220> FEATURE:
<223> OTHER INFORMATION: KLF decoy oligonucleotide

<400> SEQUENCE: 34
atccttcgcc tccttctccc aaagc                                             25

<210> SEQ ID NO 35
<211> LENGTH: 22
<212> TYPE: DNA
<213> ORGANISM: Artificial Sequence
<220> FEATURE:
<223> OTHER INFORMATION: KLF decoy oligonucleotide

<400> SEQUENCE: 35
atccttcgaa tccttccaaa gc                                                22

<210> SEQ ID NO 36
<211> LENGTH: 28
<212> TYPE: DNA
<213> ORGANISM: Artificial Sequence
<220> FEATURE:
<223> OTHER INFORMATION: KLF decoy oligonucleotide

<400> SEQUENCE: 36
gcgcacccca gcctggctca cccacgcg                                          28

<210> SEQ ID NO 37
<211> LENGTH: 37
<212> TYPE: DNA
<213> ORGANISM: Artificial Sequence
<220> FEATURE:
<223> OTHER INFORMATION: KLF decoy oligonucleotide

<400> SEQUENCE: 37
gatcctttgc ctccttcgat cctttgcctc cttcaag                                37

<210> SEQ ID NO 38
<211> LENGTH: 29
<212> TYPE: DNA
<213> ORGANISM: Artificial Sequence
<220> FEATURE:
<223> OTHER INFORMATION: KLF decoy oligonucleotide

<400> SEQUENCE: 38
ggtgtttggg agagctttgg gaggatacg                                         29

<210> SEQ ID NO 39
<211> LENGTH: 33
<212> TYPE: DNA
<213> ORGANISM: Artificial Sequence
<220> FEATURE:
<223> OTHER INFORMATION: free competitor KLF decoy oligonucleotide

<400> SEQUENCE: 39
atgcaggaga aagattggcg tagtatctac tag                                    33

<210> SEQ ID NO 40
<211> LENGTH: 33
<212> TYPE: DNA
<213> ORGANISM: Artificial Sequence
<220> FEATURE:
<223> OTHER INFORMATION: free competitor KLF decoy oligonucleotide
```

```
<400> SEQUENCE: 40
cttcatgatt ttattgcttt caaaatccaa aat                          33

<210> SEQ ID NO 41
<211> LENGTH: 30
<212> TYPE: DNA
<213> ORGANISM: Artificial Sequence
<220> FEATURE:
<223> OTHER INFORMATION: free competitor KLF decoy oligonucleotide

<400> SEQUENCE: 41
gttatgcgtt tgtagatgct ttcgttatag                              30

<210> SEQ ID NO 42
<211> LENGTH: 30
<212> TYPE: DNA
<213> ORGANISM: Artificial Sequence
<220> FEATURE:
<223> OTHER INFORMATION: free competitor KLF decoy oligonucleotide

<400> SEQUENCE: 42
ctatttcgaa acgatctaca ttggcataac                              30
```

OLIGONUCLEOTIDE DECOYS FOR THE TREATMENT OF PAIN

CROSS-REFERENCE TO RELATED APPLICATIONS

This application claims priority under 35 U.S.C. § 119(e) to U.S. Application No. 62/037,996, filed on Aug. 15, 2014, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ADDY_003_01WO_SeqList_ST25.txt. The text file is about 13 KB, was created on Aug. 14, 2015, and is being submitted electronically via EFS-Web.

BACKGROUND

Field of the Invention

The present invention relates to therapeutic agents such as double-stranded nucleic acids, termed oligonucleotide decoys, pharmaceutical compositions comprising the same, and related methods of modulating nociceptive signaling, for instance, to prevent and/or treat pain.

Description of the Related Art

Pain may be defined as an unpleasant sensory and emotional experience associated with actual or potential tissue damage, or described in terms of such damage. Chronic pain afflicts at least 40% of the U.S. population and is associated with numerous deleterious medical conditions. Persistent and highly debilitating, chronic pain is generally accompanied by weakness, sleeplessness, a lack of appetite, irritability and depression. Over time, the quality of life is profoundly affected and patients are often incapable of accomplishing the simple tasks of everyday life.

Currently used pain treatments apply a three-step pain ladder which recommends the administration of drugs as follows: non-opioids (e.g., aspirin, acetaminophen, etc.), then, as necessary, mild opioids (e.g., codeine) and finally strong opioids (e.g., morphine). Despite this arsenal of drugs, over 50% of patients with chronic pain are not effectively treated.

The ineffectiveness of current pain treatments is, inter alia, due to significant toxicity issues with existing drug therapies. Mild to severe toxicity is induced by all classes of pain drugs: non-steroidal inflammatory drugs cause gastrointestinal damage, coxibs are associated with heart failure, and opioids are responsible for numerous side effects including respiratory depression, sedation, digestive malfunctions and addiction.

Transcription factors are important factors in multiple signaling pathways and frequently control the concurrent expression of numerous genes. Many transcription factors are involved in the regulation of the expression of genes that are involved in pain including, but not limited to, BDNF, Transforming Growth factor (TGFB1), CDKN1A, GFAP, POU factors, upstream stimulatory factors (USF1, USF2), EGR1, cAMP-response element binding protein/activating transcription factors (CREB/ATF), activating protein 1 (AP1), serum response factor (SRF), promoter selective transcription factor (SP1), and the runt related transcription factor 1 (CBFA2).

Thus, there may be significant therapeutic potential in inhibiting transcription factors in order to monitor the expression of genes involved in pain. Accordingly, what is needed are selective, readily available non-toxic transcription factor inhibitors.

BRIEF SUMMARY

Embodiments of the present invention relate generally to therapeutic agents, such as oligonucleotides, which inhibit the binding of at least one Krüppel-like family (KLF) transcription factor to its endogenous transcription factor binding site(s), pharmaceutical compositions comprising such agents, and related methods of modulating nociceptive signaling, for example, to prevent and/or treat pain in a subject in need thereof. In some embodiments, the therapeutic agents are double-stranded oligonucleotides (e.g., oligonucleotide decoys), which comprise one or more transcription factor binding sites that bind to at least one KLF transcription factor.

Embodiments of the present invention therefore include oligonucleotide decoys comprising one or more transcription factor binding sites, wherein the one or more transcription factor binding sites bind to a transcription factor selected from the group consisting of KLF1, KLF2, KLF3, KLF4, KLF5, KLF6, KLF7, KLF8, KLF9, KLF10, KLF11, KLF12, KLF13, KLF14, KLF15, KLF16 and KLF17. In some embodiments, the one or more transcription factor binding sites bind to one or more transcription factors (1, 2, 3, 4, 5, etc.), selected from one or more of KLF1, KLF2, KLF3, KLF4, KLF5, KLF6, KLF7, KLF8, KLF9, KLF10, KLF11, KLF12, KLF13, KLF14, KLF15, KLF16 and KLF17.

In particular embodiments, the oligonucleotide decoys comprise a combination of at least two transcription factor binding sites, wherein each transcription factor binding site binds to a transcription factor selected from the group consisting of KLF1, KLF2, KLF3, KLF4, KLF5, KLF6, KLF7, KLF8, KLF9, KLF10, KLF11, KLF12, KLF13, KLF14, KLF15, KLF16 and KLF17. In particular embodiments, each transcription factor binding site binds to a different KLF transcription factor.

In some embodiments, the oligonucleotide decoy is about 15 to about 35 base pairs in length.

In particular embodiments, the oligonucleotide decoy comprises a first transcription factor binding site and a second transcription factor binding site, wherein the first and second transcription binding sites overlap. In certain embodiments, the first transcription factor binding site binds to KLF9, and the second transcription factor binding site binds to KLF15. In certain embodiments, the first transcription factor binding site binds to KLF9, and the second transcription factor binding site binds to KLF6.

In certain embodiments, the oligonucleotide decoy has a first transcription factor binding site, a second transcription factor binding site, and a third transcription factor binding site, wherein the first, second, and third transcription factor binding sites overlap. In specific embodiments, the first transcription factor binding site binds to KLF6, the second transcription factor binding site binds to KLF9, and the third transcription factor binding site binds to KLF15.

Certain embodiments relate to one or more population(s) of the oligonucleotide decoys described herein, wherein the population of oligonucleotide decoys provide a transcription factor binding ratio of KLF15/KLF9 equal to or less than about 0.8 or equal to or higher than about 1.0 in a standard ELISA assay.

Some embodiments relate to population(s) of the oligonucleotide decoys, wherein the population of oligonucleotide decoys provide a total transcription factor binding capacity to KLF6 and KLF9 that is equal to or higher than a predetermined value, for instance, an optical density value of about 0.2 $OD_{450}$ in a standard ELISA assay.

In some embodiments, the oligonucleotide decoy (e.g., in the population) comprises a sequence represented by Formula 1 or Formula 2:

$$a_1t_2c_3c_4T_5T_6Y_7G_8M_9M_{10}T_{11}Y_{12}Y_{13}$$
$$K_{14}Y_{15}C_{16}N_{17}H_{18}h_{19}n_{20}n_{21}V_{22}$$
$$n_{23}n_{24}y_{25}m_{26}h_{27}w_{28}b_{29}v_{30}a_{31}w_{32} \quad \text{(Formula 1; SEQ ID NO:1)}$$

$$t_1g_2t_3k_4b_5K_6K_7D_8D_9V_{10}D_{11}N_{12}S_{13}$$
$$D_{14}N_{15}B_{16}N_{17}N_{18}d_{19}v_{20}m_{21}b_{22}$$
$$v_{23}m_{24}h_{25}r_{26}m_{27}a_{28} \quad \text{(Formula 2; SEQ ID NO:2)}$$

wherein S is G or C; W is A or T; Y is T or C; D is A, G, or T; B is C, G, or T; K is T or G; M is C or A; H is C, T, or A; V is C, G, or A; R is A or G; and N is any nucleotide, wherein lower case letters can be either present or absent, and wherein the numbers in subscript represent the position of a nucleotide in the sequence.

In some embodiments, the oligonucleotide decoy comprises a sequence selected from the group consisting of SEQ ID NOs:3-35, or a variant thereof. In specific embodiments, the decoy comprises a sequence that has at least 70% identity with the sequence of SEQ ID NO:28 (16.6.5), SEQ ID NO:25 (16.6.2), SEQ ID NO:19 (17.5), SEQ ID NO:34 (T16.6-T17.5Fu1) or SEQ ID NO:35 (T16.6-T17.5 Fu2).

Certain embodiments include an oligonucleotide decoy comprising a sequence represented by Formula 1 or Formula 2:

$$a_1t_2c_3c_4T_5T_6Y_7G_8M_9M_{10}T_{11}$$
$$Y_{12}Y_{13}K_{14}Y_{15}C_{16}N_{17}H_{18} \ h_{19}n_{20}n_{21}v_{22}n_{23}n_{24}y_{25}$$
$$m_{26}h_{27}w_{28}b_{29}v_{30}a_{31}w_{32} \quad \text{(Formula 1; SEQ ID NO:1)}$$

$$t_1g_2t_3k_4b_5K_6K_7D_8D_9V_{10}D_{11}N_{12}$$
$$S_{13}D_{14}N_{15}B_{16}N_{17}N_{18}d_{19}v_{20}$$
$$m_{21}b_{22}v_{23}m_{24}h_{25}r_{26}m_{27}a_{28} \quad \text{(Formula 2; SEQ ID NO:2)}$$

wherein S is G or C; W is A or T; Y is T or C; D is A, G, or T; B is C, G, or T; K is T or G; M is C or A; H is C, T, or A; V is C, G, or A; R is A or G; and N is any nucleotide, wherein lower case letters can be either present or absent, and wherein the numbers in subscript represent the position of a nucleotide in the sequence.

In some embodiments, the decoy comprises, consists, or consists essentially of a sequence selected from the group consisting of SEQ ID NOs:3-35, or a variant thereof. In particular embodiments, the decoy comprises a sequence that has at least 70% identity with the sequence of SEQ ID NO:28 (16.6.5), SEQ ID NO:25 (16.6.2), SEQ ID NO:19 (17.5), SEQ ID NO:34 (T16.6-T17.5Fu1) or SEQ ID NO:35 (T16.6-T17.5 Fu2).

Also included are pharmaceutical compositions comprising an oligonucleotide decoy or population of decoys described herein and a pharmaceutically acceptable carrier. In certain embodiments, the oligonucleotide decoys are provided as salts, hydrates, solvates, or N-oxides derivatives.

Some embodiments include one or more kits comprising an oligonucleotide decoy or population of decoys described herein, optionally an instruction for using the oligonucleotide decoy(s).

Also included are methods for modulating the transcription of a gene present in a cell involved in nociceptive signaling comprising administering to the cell an effective amount of an oligonucleotide decoy or pharmaceutical composition described herein.

Also included are methods for modulating nociceptive signaling in a cell comprising administering to the cell an effective amount of an oligonucleotide decoy or pharmaceutical composition described herein.

Certain embodiments include methods for preventing and/or treating pain in a subject comprising administering to the subject a therapeutically effective amount of an oligonucleotide decoy or pharmaceutical composition described herein. In some embodiments, the pain is a chronic pain. In particular embodiments, the pain is neuropathic pain. In some embodiments, the pain is associated with inflammation. In certain embodiments, the pain is associated with central nervous system or visceral disorder. In specific embodiments the pain is neuropathic pain associated with inflammation.

Also included are methods for modulating nociceptive signaling in a cell comprising administering to the cell a therapeutically effective amount of a therapeutic agent, wherein the therapeutic agent inhibits binding of a transcription factor to its transcription factor binding site, wherein the transcription factor is selected from the group consisting of KLF1, KLF2, KLF3, KLF4, KLF5, KLF6, KLF8, KLF9, KLF10, KLF11, KLF12, KLF13, KLF14, KLF15, KLF16 and KLF17.

In some embodiments, the therapeutic agent provides a binding ratio of KLF15/KLF9 equal to or less than about 0.8 or equal to or higher than about 1.0 in a standard ELISA assay (e.g., based on $OD_{450}$ values or equivalent standard ELISA measurement units). In particular embodiments, the therapeutic agent provides a total transcription factor binding capacity to KLF6 and KLF9 that is equal to or higher than an optical density value of about 0.2 $OD_{450}$ in a standard ELISA assay, or a comparable binding level using equivalent standard ELISA measurement units.

Also included are methods for treating pain in a subject comprising administering to the subject a therapeutically effective amount of a therapeutic agent, wherein the therapeutic agent inhibits binding of a transcription factor to its transcription binding site, wherein the transcription factor is selected from the group consisting of KLF1, KLF2, KLF3, KLF4, KLF5, KLF6, KLF8, KLF9, KLF10, KLF11, KLF12, KLF13, KLF14, KLF15, KLF16 and KLF17. In some embodiments, the therapeutic agent provides a binding ratio of KLF15/KLF9 equal to or less than about 0.8 or equal to or higher than about 1.0 in a standard ELISA assay. In certain embodiments, the therapeutic agent provides a total transcription factor binding capacity to KLF6 and KLF9 that is equal to or higher than an optical density value of about 0.2 $OD_{450}$ in a standard ELISA assay. In particular embodiments, the pain is neuropathic pain, pain associated with inflammation, and/or neuropathic pain associated with inflammation.

BRIEF DESCRIPTION OF THE DRAWINGS

FIG. 1 shows the KLF binding characteristics of certain of the oligonucleotide decoys, relative to control KLF decoys (highlighted in gray). Binding values to KLF6, KLF9, and KLF15 are presented as mean and SEM $OD_{450}$ values from the in vitro ELISA binding assay described in Example 1. The corresponding N is also listed. The efficacy for treating neuropathic and/or neuro-inflammatory pain is presented as percentage (%) of pain reduction relative to control during the testing period (~4-8 weeks total, ~2-4 weeks following treatment depending on the study) of the corresponding animal studies. N/A=Non-applicable.

FIG. 4A-C show the efficacy level of certain of the oligonucleotide decoys in relation to their ratio of KLF15/ KLF9 binding (4A), coefficients of linear correlation between the efficacy for treating chronic neuropathic pain and the binding parameters to KLF6, KLF9 and KLF15 (4B), and a linear regression of efficacy levels for the population of the tested decoys in relation to their KLF15/ KLF9 binding ratios, excluding ratios ~0.9 (4C). The efficacy level of each decoy was measured as the percentage of pain relief vs. control in the SNI model of chronic pain during the testing period (~4-8 weeks total, ~2-4 weeks following treatment depending on the study).

FIGS. 5A-C show the efficacy level of certain of the oligonucleotide decoys in relation to their combined binding to KLF6, KLF9 and KLF15 (5A), coefficients of linear correlation between the efficacy for treating chronic neuro-inflammatory pain and the binding parameters to KLF6, KLF9 and KLF15 (5B), and a linear regression of efficacy level for the population of tested decoys in relation to their total binding capacity to KLF6 and KLF9, as indicated by their 1/(KLF6+KLF9) binding ratios (5C). The efficacy level of each decoy was measured as the percentage of pain reduction vs. control in the CCI model of chronic pain during the testing period (~4-8 weeks total, ~2-4 weeks following treatment depending on the study).

DETAILED DESCRIPTION

Figure 2A:
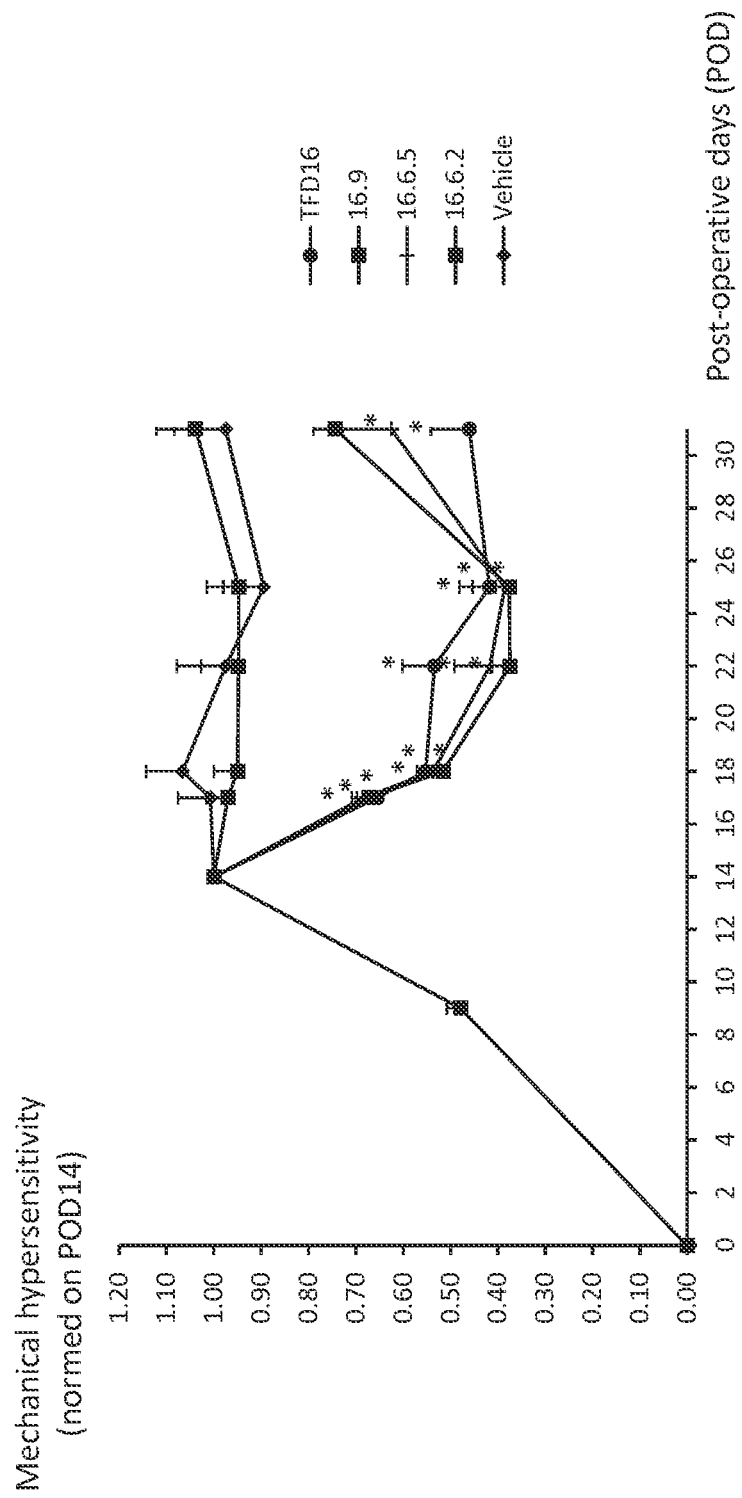
FIGS. 2A-B show the efficacy of certain of the oligonucleotide decoys in the spared nerve injury (SNI) model of chronic neuropathic pain. Pain was measured as mechanical hypersensitivity using repetitive von Frey filaments. Oligonucleotide decoys (200 nmoles) or vehicle were injected once intrathecally at post-operative day 14 (POD14). Mean+ SEM values of total responses to von Frey stimulations were normalized on the baseline pain values measured at POD14 prior to the injection of vehicle or decoys; pre-injection data before POD14 are combined across groups, T-test vs. vehicle at a given time-point: * p≤0.05, decoy vs. vehicle data distribution post-treatment (POD 17-POD31): p≤0.001 for TFD16, 16.6.2, 16.6.5, TFD17, 17.5, p=0.005 for 17.1, p=0.39 for 16.9 and p=0.46 for 17.9; n=4 rats per testing group. The X-axis shows post-operative days (POD).

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.
Definitions The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight, or length.

"Binding," as used in the context of transcription factors binding to therapeutic agents such as oligonucleotide decoys, refers to a direct interaction (e.g., non-covalent bonding between the transcription factor and the oligonucleotide decoy, including hydrogen-bonding, van der Waals bonding, etc.) between a transcription factor and an oligonucleotide decoy. Accordingly, a therapeutic agent such as an oligonucleotide that does not bind to a transcription factor does not directly interact with said transcription factor, and vice versa.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of:" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

"Chronic" refers to a period of time comprising months (e.g., at least two months) or years.

"Homology" refers to the percentage number of nucleotides that are identical or constitute conservative substitutions. Homology may be determined using sequence comparison programs such as EMBOSS Pairwise Alignment Algorithm (available from the European Bioinformatics Institute (EBI)), the ClustalW program (also available from the European Bioinformatics Institute (EBI)), or the BLAST program (BLAST Manual, Altschul et al., Natl Cent. Biotechnol. Inf., Natl Lib. Med. (NCIB NLM NIH), Bethesda, Md., and Altschul et al., (1997) NAR 25:3389 3402), or GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

The term "modulate" includes an "increase" or "decrease" an one or more quantifiable parameters, optionally by a defined and/or statistically significant amount. By "increase" or "increasing," "enhance" or "enhancing," or "stimulate" or "stimulating," refers generally to the ability of one or more agents such as oligonucleotide decoys to produce or cause a greater physiological or cellular response in a cell or a subject, such as the activity of a transcription factor (e.g., gene expression), relative to the response caused by either no agent or a control compound. Relevant physiological or cellular responses (in vivo or in vitro) will be apparent to persons skilled in the art. An "increased" or "enhanced" amount or response may be "statistically significant" relative to an amount or response produced by no agent or a control composition, and may include an increase that is 1.1, 1.2, 2, 3, 4, 5, 6, 7, 8, 9, 10, 15, 20, 30, 40, 50 or more times (e.g., 500, 1000 times) (including all integers and ranges between and above 1, e.g., 1.5, 1.6, 1.7. 1.8) the amount or response produced by either no agent or a control compound. The term "reduce" or "inhibit" may relate generally to the ability of one or more agents such as oligonucleotide decoys to "decrease" a relevant physiological or cellular response in a cell or a subject, such as the activity of a transcription factor (e.g., gene expression), a physiological process (e.g., nociceptive signaling), or a symptom of a disease or condition described herein (e.g., pain), relative to the response caused by either no agent or a control compound. Relevant physiological or cellular responses (in vivo or in vitro) will be apparent to persons skilled in the art and can be measured according to routine techniques. A "decrease" in a response may be "statistically significant" as compared to the response produced by no agent or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers and ranges in between.

"Modulation of gene expression level" includes any change in gene expression level, including an induction or activation (e.g., an increase in gene expression), an inhibition or suppression (e.g., a decrease in gene expression), or a stabilization (e.g., prevention of the up-regulation or down-regulation of a gene that ordinarily occurs in response to a stimulus, such as a pain-inducing stimulus).

"Nociceptive signaling" refers to molecular and cellular mechanisms involved in the detection of a noxious stimulus or of a potentially harmful stimulus, which leads to the perception of pain. Particular examples include neurotransmitter synthesis and release, neurotransmitter-induced signaling, membrane depolarization, and related intra-cellular and inter-cellular signaling events.

"Pain" refers to an unpleasant sensory and emotional experience that is associated with actual or potential tissue damage or described in such terms. All of the different manifestations and qualities of pain, including mechanical pain (e.g., induced by a mechanical stimulus or by body motion), temperature-induced pain (e.g., pain induced by hot, warm and/or cold temperatures), and chemically-induced pain (e.g., pain induced by a chemical). In certain embodiments, pain is chronic, sub-chronic, acute, or sub-acute. In certain embodiments, pain features hyperalgesia (e.g., an increased sensitivity to a painful stimulus) and/or allodynia (e.g., a painful response to a usually non-painful stimulus). In certain embodiments, pain is pre-existing in a patient. In other embodiments, pain is iatrogenic, induced in a patient (e.g., post-operative pain).

"Preventing" or "prevention" includes (1) a reduction in the risk of acquiring a disease or disorder (e.g., causing at least one of the clinical symptoms of a disease not to develop in a patient that may be exposed to or predisposed to the disease but does not yet experience or display symptoms of the disease), and/or (2) a reduction in the likely severity of a symptom associated with a disease or disorder (e.g., reducing the likely severity of at least one of the clinical symptoms of a disease in a patient that may be exposed to or predisposed to the disease but does not yet experience or display symptoms of the disease).

The terms "sequence identity" or, for example, comprising a "sequence 50% identical to," as used herein, refer to the extent that sequences are identical on a nucleotide-by-nucleotide basis over a window of comparison. Thus, a "percentage of sequence identity" may be calculated by comparing two optimally aligned sequences over the window of comparison, determining the number of positions at which the identical nucleic acid base (e.g., A, T, C, or G) occurs in both sequences to yield the number of matched positions, dividing the number of matched positions by the total number of positions in the window of comparison (i.e., the window size), and multiplying the result by 100 to yield the percentage of sequence identity. In some embodiments, optimal alignment of sequences for aligning a comparison window may be conducted by using the EMBOSS Pairwise Alignment Algorithm (available from the European Bioinformatics Institute (EBI)), the ClustalW program (also available from the European Bioinformatics Institute (EBI)), or the BLAST program (BLAST Manual, Altschul et al., Natl Cent. Biotechnol. Inf., Natl Lib. Med. (NCIB NLM NIH), Bethesda, Md., and Altschul et al., (1997) NAR 25:3389 3402). In certain embodiments, the alignment of sequences for aligning a comparison window is conducted against the entire length of the reference sequence (e.g., from the Sequence Listing). In some embodiments, the alignment of sequences for aligning a comparison window is conducted against a portion of the reference sequence, for example, about, at least about, or no more than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 contiguous nucleotides of the reference sequence.

A "subject" or a "subject in need thereof" or a "patient" includes a mammalian subject such as a primate or human subject.

"Sub-acute" refers to a period of time comprising hours (e.g., 1-24 hours, including all integers and ranges in between).

"Sub-chronic" refers to a period of time comprising days or months (e.g., less than two or three months).

"Treating" or "treatment" of any disease or disorder refers, in some embodiments, to ameliorating the disease or disorder (e.g., arresting or reducing the development of the disease or at least one of the clinical symptoms thereof). In some embodiments, "treating" or "treatment" refers to ameliorating at least one physical and/or biological parameter, which may not be discernible by the patient. In certain embodiments, "treating" or "treatment" refers to inhibiting the disease or disorder, either physically, (e.g., stabilization of a discernible symptom), physiologically, (e.g., stabilization of a physical parameter) or both. In some embodiments, "treating" or "treatment" refers to delaying the onset of the disease or disorder. "Treatment" or "prophylaxis" does not necessarily indicate complete eradication, cure, or prevention of the disease or condition, or associated symptoms thereof.

"Therapeutically effective amount" means the amount of a compound that, when administered to a patient, is sufficient to effect such treatment of a particular disease or condition. The "therapeutically effective amount" will vary depending on the compound, the disease, the severity of the disease, and the age, weight, etc., of the patient to be treated.

Oligonucleotide Decoys and Other Therapeutic Agents

Embodiments of the present invention relate generally to therapeutic agents that inhibit binding of at least one transcription factor to at least one of its (endogenous) transcription binding site. Particular examples include oligonucleotide decoys that comprise one or more transcription binding sites that bind to at least one transcription factor, and thereby alter the ability of the transcription factor(s) to modulate gene expression. In certain embodiments, the transcription factor is one or more members of the Krüppel-like family (KLFs) of transcription factors, examples of which include KLF1, KLF2, KLF3, KLF4, KLF5, KLF6, KLF7, KLF8, KLF9, KLF10, KLF11, KLF12, KLF13, KLF14, KLF15, KLF16 and KLF17.

Thus, certain embodiments include an oligonucleotide decoy that comprises one or more (e.g., 1, 2, 3, 4, 5, etc.) transcription factor binding sites, where the one or more transcription factor binding site binds to a transcription factor selected from the group consisting of KLF1, KLF2, KLF3, KLF4, KLF5, KLF6, KLF7, KLF8, KLF9, KLF10, KLF11, KLF12, KLF13, KLF14, KLF15, KLF16 and KLF17.

Also included are oligonucleotide decoys that comprise a combination of at least two (e.g., 2, 3, 4, 5, etc.) transcription factor binding sites, wherein each transcription factor binding site binds to a transcription factor selected from the group consisting of KLF1, KLF2, KLF3, KLF4, KLF5, KLF6, KLF7, KLF8, KLF9, KLF10, KLF11, KLF12, KLF13, KLF14, KLF15, KLF16 and KLF17. Particular examples of combinations of transcription factor binding sites include those that bind to KLF6/KLF9, KLF9/KLF15, or KLF6/KLF9/KLF15.

The term "oligonucleotide" includes any double-stranded or substantially double-stranded, nucleic acid-containing polymer generally less than approximately 200 nucleotides (or 100 base pairs) and including, but not limited to, DNA, RNA and RNA-DNA hybrids.

In some embodiments, the oligonucleotide is about, at least about, or no more than about, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nucleotides in length (including all integers and ranges in between), and optionally comprises about, at least about, or no more than about, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 base-paired nucleotides (including all integers and ranges in between). In particular embodiments, the oligonucleotide decoy is about 15 to about 35 base pairs in length.

In some embodiments, the oligonucleotide decoy comprises a first transcription factor binding site and a second transcription binding site, optionally wherein the first transcription binding site and the second transcription binding site overlap. In specific embodiments, the first transcription factor binding site binds to KLF9 and the second transcription factor binding site binds to KLF15. In particular embodiments, the first transcription factor binding site binds to KLF9 and the second transcription factor binding site binds to KLF6.

Also included are oligonucleotide decoys that have a first transcription factor binding site, a second transcription factor binding site, and a third transcription factor binding site, optionally wherein the first, second, and third transcription binding sites overlap. In specific embodiments, the first transcription factor binding site binds to KLF6, the second transcription factor binding site binds to KLF9, and the third transcription factor binding site binds to KLF15.

In certain embodiments, the oligonucleotide decoy (e.g., the sense strand of the decoy) comprises, consists, or consists essentially of a sequence (e.g., double-stranded sequence) represented by Formula 1 or Formula 2, shown in Table 1 below, or a variant thereof, or a complement thereof (e.g., the antisense sequence).

TABLE 1

| Sequence name | Sequence (5' to 3') | SEQ ID NO: |
|---|---|---|
| Formula 1 | $a_1t_2c_3c_4T_5T_6Y_7G_8M_9M_{10}T_{11}Y_{12}Y_{13}K_{14}Y_{15}C_{16}N_{17}H_{18}h_{19}n_{20}n_{21}v_{22}n_{23}n_{24}y_{25}m_{26}h_{27}w_{28}$ $b_{29}v_{30}a_{31}w_{32}$ | 1 |
| Formula 2 | $t_1g_2t_3k_4b_5K_6K_7D_8D_9V_{10}D_{11}N_{12}S_{13}D_{14}N_{15}B_{16}N_{17}N_{18}d_{19}v_{20}m_{21}b_{22}v_{23}m_{24}h_{25}r_{26}m_{27}a_{28}$ | 2 | wherein S is G or C; W is A or T; Y is T or C; D is A, G, or T; B is C, G, or T; K is T or G; M is C or A; H is C, T, or A; V is C, G, or A; R is A or G; and N is any nucleotide, wherein lower case letters can be either present or absent, and wherein the numbers in subscript represent the position of a nucleotide in the sequence.

In specific embodiments, the oligonucleotide decoy (e.g., the sense strand of the decoy) comprises, consists, or consists essentially of a sequence in Table 2 below, or a variant thereof, or a complement thereof (e.g., the antisense sequence).

TABLE 2

| Sequence name | Sequence (5' to 3') | SEQ ID NO: |
|---|---|---|
| 16.0 | TTTGCCTCCTTCGATCCC | 3 |
| 16.1 | ATCCTTTGCCTCCTTCGA | 4 |
| 16.2 | ATCCTTTGCCTCCTTCCCTTTGCCTCCTTCAA | 5 |
| 16.3 | CCTTTGCCTCCTTCCCTTTGCCTCCTTC | 6 |
| 16.4 | ATCCTTTGCCTCCTTCGAAGGAGGCAAAGGAT | 7 |
| 16.5 | ATCCTTTGCCTCCTTCCTTTGCCTCCTTCAA | 8 |
| 16.6 | ATCCTTTGCCTCCTTCGCCTCCTTCAA | 9 |
| 16.7 | CCTTTGCCTCCTTCGCCTCCTTC | 10 |
| 16.8 | ATCCTTTGCCTCCTTCTCCTTCAA | 11 |
| 16.9 | ATCCTTTGCCTTTGCCTCCTTCAA | 12 |
| 16.10 | CCTTTGCCTTTGCCTCCTTC | 13 |
| 17.0 | TGTTTGGGAGAGCTT | 14 |
| 17.1 | GCTTTGGGAGGATAC | 15 |
| 17.2 | TGGGAGAGCTTTGGGA | 16 |
| 17.3 | TGTTTGGGAGATTTGGGAGGATAC | 17 |
| 17.4 | TTTGGGAGATTTGGGAGGAT | 18 |
| 17.5 | TGTTTGGGAGAATCCTCCCAAAGC | 19 |
| 17.6 | TTTGGGAGAATCCTCCCAAA | 20 |
| 17.7 | TGTTTGGGAGAGCTATCCTCCCAAAGC | 21 |
| 17.8 | TTTGGGAGAGCTATCCTCCCAAA | 22 |
| 17.9 | TGTTTGGGAGAGGGAGGATAC | 23 |
| 17.10 | TGTTTGGGTTTGGGAGGATAC | 24 |
| 16.6.2 | CCTTTGCCTCCTTCGCCTCCTTCAA | 25 |
| 16.6.3 | TCCTTTGCCTCCTTCGCCTCCTTCA | 26 |
| 16.6.4 | CCTTTGCCTCCTTCGCCTCCTTCA | 27 |
| 16.6.5 | ATCCTTCGCCTCCTTCAA | 28 |
| 16.6.6 | ATCCTTCGCCTTCGCCTCCTTCAA | 29 |
| 16.6.7 | ATCCTTCGCCTCCTTCGCCTCCTTCAA | 30 |

TABLE 2-continued

| Sequence name | Sequence (5' to 3') | SEQ ID NO: |
|---|---|---|
| 17.5.1 | TGTTTGGGAGAATCCTCCCAAA | 31 |
| 17.5.2 | TTTGGGAGAATCCTCCCAAAGC | 32 |
| 17.5.3 | GTTTGGGAGAATCCTCCCAAAG | 33 |
| T16.6-T17.5 Fu1 | ATCCTTCGCCTCCTTCTCCCAAAGC | 34 |
| T16.6-T17.5 Fu2 | ATCCTTCGAATCCTTCCAAAGC | 35 |

In the formulas and sequences described herein, "A" is an adenine nucleotide, "C" is a cytosine nucleotide, "G" is a guanine nucleotide, "T" is a thymine nucleotide, and "N" can be any nucleotide, preferably A, C, G, or T. Although the formulas and sequences show a single strand, it should be understood that a complementary antisense strand is included as part of the structure of the oligonucleotide decoys. In certain embodiments, any one or more "T" can be a "U" or uracil nucleotide.

Certain oligonucleotide decoys thus comprise, consist, or consist essentially of a sequence in Table 1 or Table 2 (e.g., SEQ ID NOS:1-35) or a variant or contiguous or non-contiguous portion(s) thereof. For instance, certain oligonucleotide decoys comprise about or at least about 10, 11, 12, 13, 14, 15, 16, 17, 18, 19, 20, 21, 22, 23, 24, 25, 26, 27, 28, 29, 30, 31, 32, 33, 34, or 35 contiguous or non-contiguous nucleotides of any of the targeting sequences in Table 1 or Table 2 (e.g., SEQ ID NOS:1-35), and which bind to one or more KLF transcription factors described herein (e.g., KLF1, KLF2, KLF3, KLF4, KLF5, KLF6, KLF7, KLF8, KLF9, KLF10, KLF11, KLF12, KLF13, KLF14, KLF15, KLF16, KLF17). For non-contiguous portions, intervening nucleotides can be deleted or substituted with a different nucleotide, or intervening nucleotides can be added. Additional examples of variants include oligonucleotide decoys having at least or at least about 70% sequence identity or homology (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology) to the entire length or a contiguous portion of a sequence in Table 1 or Table 2 (e.g., SEQ ID NOS:1-35), and which bind to one or more KLF transcription factors described herein (e.g., KLF1, KLF2, KLF3, KLF4, KLF5, KLF6, KLF7, KLF8, KLF9, KLF10, KLF11, KLF12, KLF13, KLF14, KLF15, KLF16, KLF17). In some embodiments, the contiguous portion is about, at least about, or no more than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 contiguous nucleotides of a sequence in Table 1 or Table 2 (e.g., SEQ ID NOS:1-35).

An oligonucleotide decoy having a certain percent (e.g., 65%, 70%, 75%, 80%, 85%, 90%, 95%, or 99%) of sequence identity with another sequence means that, when aligned, that percentage determines the level of correspondence of bases arrangement in comparing the two sequences. This alignment and the percent homology or identity can be determined using any suitable software program known in the art that allows local alignment. In some embodiments, such programs include but are not limited to the EMBOSS Pairwise Alignment Algorithm (available from the European Bioinformatics Institute (EBI)), the ClustalW program (also available from the European Bioinformatics Institute (EBI)), or the BLAST program (BLAST Manual, Altschul et al., Natl Cent. Biotechnol. Inf., Natl Lib. Med. (NCIB NLM NIH), Bethesda, Md., and Altschul et al., (1997) NAR 25:3389 3402).

As noted above, one skilled in the art will recognize that the sequences encompassed by the invention include those that are fully or partially complementary to the sequences described herein, including those that hybridize under stringent hybridization conditions with an exemplified sequence (e.g., Tables 1 and 2; SEQ ID NOs:1-35). A nucleic acid is hybridizable to another nucleic acid when a single stranded form of the nucleic acid can anneal to the other single stranded nucleic acid under appropriate conditions of temperature and solution ionic strength. Hybridization conditions are well known in the art. In some embodiments, annealing may occur during a slow decrease of temperature from a denaturing temperature (e.g., 100° C.) to room temperature in a salt containing solvent (e.g., Tris-EDTA buffer).

Also included are populations of oligonucleotide decoys, including those which provide a transcription factor binding ratio to a combination of KLF transcription factors (e.g., KLF15/KLF9), and/or a total transcription binding capacity to one or more (e.g., 1, 2, 3, 4, 5, etc.) KLF transcription factors (e.g., KLF6+KLF9), which is defined relative to a predetermined amount. In some embodiments, the transcription factor binding ratio or total transcription binding capacity is about equal to, less than, or higher than a predetermined level or amount. A "predetermined level" for defining a relative binding ratio or a total binding capacity can be established using a variety of techniques, such as standard ELISA assays (see the Examples).

For example, in specific embodiments, the population of oligonucleotide decoys provides a transcription factor binding ratio of KLF15/KLF9 that is equal to or less than about 0.8 or equal to or higher than about 1.0, based on $OD_{450}$ values (or equivalent standard ELISA measurement units, e.g., fluorescence) from a standard ELISA assay (see the Examples). In specific embodiments, the transcription factor binding ratio of KLF15/KLF9 is equal to or less than about 0.8, 0.7, 0.6, 0.5, 0.4, 0.3, 0.2, 0.1, 0.05, 0.01 or less (including all ranges and integers in between) based on $OD_{450}$ values from a standard ELISA assay. In some embodiments, the transcription factor binding ratio of KLF15/KLF9 is equal to or higher than about 1.0, 1.1, 1.2, 1.3, 1.4, 1.5, 1.6, 1.7, 1.8, 1.9, 2.0, 2.5, 3.0, 3.5, 4.0, 4.5, 5.0, 6.0, 7.0, 8.0, 9.0, or 10.0, or higher (including all ranges and integers in between) based on $OD_{450}$ values (or equivalent standard ELISA measurement units) from a standard ELISA assay.

In some embodiments, the population of oligonucleotide decoys provides a total transcription factor binding capacity to KLF6 and KLF9 that is equal to or higher than a predetermined amount. In some instances, the predetermined amount is an optical density value (or an equivalent standard ELISA measurement unit, e.g., fluorescence) of about 0.2 $OD_{450}$ or higher as measured in a standard ELISA assay (see the Examples). In some embodiments, the predetermined amount or the total transcription factor binding capacity to KLF6 and KLF9 is equal to or higher than about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, or higher (including all ranges and integers in between) based on $OD_{450}$ values (or equivalent standard ELISA measurement units) from a standard ELISA assay.

In some embodiments, the population of oligonucleotide decoys provides a total transcription factor binding capacity to KLF6 and KLF9 that is equal to or less than a predetermined amount. In some embodiments, the predetermined amount or the total transcription factor binding capacity to KLF6 and KLF9 is indicated as 1/(KLF6+KLF9) based on an optical density value (or an equivalent standard ELISA measurement unit, e.g., fluorescence) from a standard ELISA assay (see the Examples). For instance, in particular embodiments, the total transcription factor binding capacity to KLF6 and KLF9 (as indicated by 1/(KLF6+KLF9) is about 5 or less based on $OD_{450}$ values (or an equivalent standard ELISA measurement unit) from a standard ELISA assay. In some embodiments, the total transcription factor binding capacity to KLF6 and KLF9 (as indicated by 1/(KLF6+KLF9)) is equal to or less than about 5, 4, 3, 2, 1, 0.5, 0.1, or less (including all ranges and integers in between) based on $OD_{450}$ values (or an equivalent standard ELISA measurement unit) from a standard ELISA assay.

The population of oligonucleotide decoys can be composed of one oligonucleotide decoy, or a combination of two or more (e.g., 2, 3, 4, 5, etc.) oligonucleotide decoys. In certain embodiments, the population of oligonucleotide decoys is composed of one oligonucleotide decoy with a single KLF transcription factor binding site. In some embodiments, the population of oligonucleotide decoys is composed of one oligonucleotide decoy with combination of at least two (e.g., 2, 3, 4, 5, etc.) transcription factor binding sites, which bind to the same or different (e.g., two or at least two different) KLF transcription factors. In some embodiments, the population of oligonucleotide decoys comprises one oligonucleotide decoy with combination of at least three (e.g., 3, 4, 5, etc.) transcription factor binding sites, which bind to the same or different (e.g., three or at least three different) KLF transcription factors. Other combinations will be apparent to persons skilled in the art.

Generally, the oligonucleotide decoys disclosed herein may be used to bind and, e.g., thereby inhibit, transcription factors that modulate the expression of genes involved nociceptive signaling and/or a subject's (e.g., patient's) perception of pain. An oligonucleotide decoy that is designed to bind to a specific transcription factor has a nucleic acid sequence mimicking the endogenous genomic DNA sequence normally bound by the transcription factor. Accordingly, in some aspects the oligonucleotide decoys disclosed herein inhibit a necessary step for gene expression and regulation. Further, the oligonucleotide decoys disclosed herein may bind to one or a number of different transcription factors.

The term oligonucleotide encompasses sequences that include any of the known base analogs of DNA and RNA including, but not limited to, 2,6-diaminopurine, 5-carboxymethylaminomethyl-2-thiouracil, 5-carboxymethylaminomethyluracil, dihydrouracil, inosine, uracil-5-oxyacetic acid, N6-isopentenyladenine, 1-methyladenine, N-uracil-5-oxyacetic acid methylester, queosine, 2-thiocytosine, 5-bromouracil, methylphosphonate, phosphorodithioate, ormacetal, 3'-thioformacetal, nitroxide backbone, sulfone, sulfamate, morpholino derivatives, locked nucleic acid (LNA) derivatives, and/or peptide nucleic acid (PNA) derivatives. In some embodiments, the oligonucleotide is composed of two complementary single-stranded oligonucleotides that are annealed together. In some embodiments, the oligonucleotide is composed of one single-stranded oligonucleotide that forms intramolecular base pairs to create a substantially double-stranded structure.

In some embodiments, the oligonucleotide decoys disclosed herein are chemically modified by methods well known to the skilled artisan (e.g., incorporation of phosphorothioate, methylphosphonate, phosphorodithioate, phosphoramidates, carbonate, thioether, siloxane, acetamidate or carboxymethyl ester linkages between nucleotides), for example, to prevent degradation by nucleases within cells and/or in extra-cellular fluids (e.g., serum, cerebrospinal fluid). In some embodiments, the oligonucleotide decoys are designed to form hairpin and dumbbell structures, which can also prevent or hinder nuclease degradation. In particular embodiments, the oligonucleotide decoys are inserted as a portion of a larger plasmid capable of episomal maintenance or constitutive replication in the target cell in order to provide longer-term, enhanced intracellular exposure to the decoy sequence and/or reduce its degradation. Accordingly, any chemical modification or structural alteration known in the art to enhance oligonucleotide stability is within the scope of the present disclosure. In some embodiments, the oligonucleotide decoys disclosed herein may be attached, for example, to polyethylene glycol polymers, peptides (e.g., a protein translocation domain) or proteins which improve the therapeutic effect of oligonucleotide decoys. Such modified oligonucleotide decoys may preferentially traverse the cell membrane.

The oligonucleotide decoys described herein may generally be utilized as the free acid or free base. Alternatively, the oligonucleotide decoys may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, calcium, potassium, magnesium, barium and calcium), as well as the ammonium ion and substituted derivatives thereof (e.g., dibenzylammonium, benzylammonium, 2-hydroxyethylammonium, and the like). Thus, the term "pharmaceutically acceptable salt" is intended to encompass any and all acceptable salt forms.

Prodrugs are also included. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the oligonucleotide decoys described herein. Further, in the case of a carboxylic acid (—COOH), esters may be employed, such as methyl esters, ethyl esters, and the like.

In certain embodiments, the oligonucleotide decoys are provided as salts, hydrates, solvates, or N-oxide derivatives. In certain embodiments, the oligonucleotide decoys are provided in solution (e.g., a saline solution having a physiologic pH) or in lyophilized form. In some embodiments, the oligonucleotide decoys are provided in liposomes.

The oligonucleotide decoys described herein may be made by conventional methods known in the art and thus are well within the knowledge of the skilled artisan. The activity of oligonucleotide decoys and variants thereof can be assayed according to routine techniques in the art (see the Examples). In particular embodiments, the oligonucleotide decoy is a synthetic oligonucleotide (i.e., a chemically-synthesized, non-naturally-occurring oligonucleotide).

Also included are non-oligonucleotide-based therapeutic agents, including those that inhibit binding of a transcription factor to its endogenous transcription binding site, for instance, by specifically binding to a KLF transcription factor, or by specifically binding to its endogenous transcription factor binding site (e.g., by mimicking the KLF transcription factor binding site). Examples of therapeutic agents include binding agents such as antibodies, small molecules, peptides, adnectins, anticalins, Darpins, anaphones, and aptamers, which exhibit binding specificity for a KLF transcription factor, e.g., a KLF factor transcription factor binding site domain, or which exhibit binding specificity for an endogenous KLF transcription factor binding site.

A binding agent is said to "exhibit binding specificity for," "specifically bind to," a KLF polypeptide (e.g., a transcription factor binding domain thereof), or an endogenous KLF transcription factor binding site (e.g., double-stranded DNA sequence), if it reacts at a detectable level (within, for example, an ELISA assay) with the polypeptide or nucleic acid, and does not react detectably in a significant (e.g., statistically significant) manner with unrelated structures under similar conditions.

The term "antibody" relates to an immunoglobulin whether natural or partly or wholly synthetically produced. The term also covers any polypeptide or protein having a binding domain which is, or is homologous to, an antigen-binding domain. CDR grafted antibodies are also contemplated by this term. The term "antigen-binding portion of an antibody," "antigen-binding fragment," "antigen-binding domain," "antibody fragment" or a "functional fragment of an antibody" are used interchangeably in the present invention to include one or more fragments of an antibody that retain the ability to specifically bind to an antigen (see, e.g., Holliger et al., Nature Biotech. 23 (9): 1126-1129 (2005)).

Antibodies may be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest may be prepared, for example, using the technique of Kohler and Milstein, Eur. J.

Immunol. 6:511-519, 1976, and improvements thereto. Also included are methods that utilize transgenic animals such as mice to express human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Particular examples include the VELOCIMMUNE® platform by REGENEREX® (see, e.g., U.S. Pat. No. 6,596,541). Antibodies can also be generated or identified by the use of phage display or yeast display libraries (see, e.g., U.S. Pat. No. 7,244,592; Chao et al., Nature Protocols. 1:755-768, 2006).

As noted above, "peptides" that inhibit binding of a KLF transcription factor to its transcription factor binding site are included as binding agents. The term peptide typically refers to a polymer of amino acid residues and to variants and synthetic analogues of the same. In certain embodiments, the term "peptide" refers to relatively short polypeptides, including peptides that consist of about 3, 4, 5, 6, 7, 8, 9, 10, 11, 12, 13, 14, 15, 16, 17, 18, 19, 20, 25, 30, 31, 32, 33, 34, 35, 36, 37, 38, 39, 40, 41, 42, 43, 44, 45, 46, 47, 48, 49, 50 or more amino acids, including all integers and ranges (e.g., 5-10, 8-12, 10-15, 15-20, 20-25, 25-30, 30-40, 40-50) in between, and which, for example, bind to one or more regions of a KLF transcription factor, e.g., a transcription factor binding domain, or mimic the KLF transcription factor by binding to at least one of its endogenous transcription factor binding sites. Peptides can be composed of naturally-occurring amino acids and/or non-naturally occurring amino acids.

As noted above, the present invention includes small molecules that inhibit binding of a KLF transcription factor to its transcription factor binding site. A "small molecule" refers to an organic or inorganic compound that is of synthetic or biological origin, but is typically not a polymer. Organic compounds include a large class of chemical compounds whose molecules contain carbon, typically excluding those that contain only carbonates, simple oxides of carbon, or cyanides. A "polymer" refers generally to a large molecule or macromolecule composed of repeating structural units, which are typically connected by covalent chemical bond. In certain embodiments, a small molecule has a molecular weight of less than 1000-2000 Daltons, typically between about 300 and 700 Daltons, and including about 50, 100, 150, 200, 250, 300, 350, 400, 450, 500, 550, 500, 650, 600, 750, 700, 850, 800, 950, 1000 or 2000 Daltons.

Aptamers that inhibit binding of a KLF transcription factor to its transcription factor binding site are also included as binding agents (see, e.g., Ellington et al., Nature. 346, 818-22, 1990; and Tuerk et al., Science. 249, 505-10, 1990). Examples of aptamers included nucleic acid aptamers (e.g., DNA aptamers, RNA aptamers) and peptide aptamers. Nucleic acid aptamers refer generally to nucleic acid species with secondary and tertiary structures that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. See, e.g., U.S. Pat. Nos. 6,376,190; and 6,387,620 Hence, included are nucleic acid aptamers that bind to one or more regions of a KLF transcription factor, e.g., a transcription factor binding domain, or which bind to at least one of its endogenous transcription factor binding sites.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments may utilize the bacterial protein Thioredoxin-A as a scaffold protein, the variable loop being inserted within the reducing active site (-Cys-Gly-Pro-Cys- loop in the wild protein), with the two cysteine lateral chains being able to form a disulfide bridge. Methods for identifying peptide aptamers are described, for example, in U.S. Application No. 2003/0108532. Hence, included are peptide aptamers that bind to one or more regions of a KLF transcription factor, e.g., a transcription factor binding domain, or which bind to at least one of its endogenous transcription factor binding sites. Peptide aptamer selection can be performed using different systems known in the art, including the yeast two-hybrid system.

Also included are ADNECTINS™, AVIMERS™, and ANTICALINS that specifically bind to KLF transcription factor. ADNECTINS™ refer to a class of targeted biologics derived from human fibronectin, an abundant extracellular protein that naturally binds to other proteins. See, e.g., U.S. Application Nos. 2007/0082365; 2008/0139791; and 2008/0220049. ADNECTINS™ typically consists of a natural fibronectin backbone, as well as the multiple targeting domains of a specific portion of human fibronectin. The targeting domains can be engineered to enable an Adnectin™ to specifically recognize a therapeutic target of interest, such as a KLF transcription factor polypeptide, or a fragment thereof, e.g., a transcription factor binding domain, or at least one of its endogenous transcription factor binding sites.

AVIMERS™ refer to multimeric binding proteins or peptides engineered using in vitro exon shuffling and phage display. Multiple binding domains are linked, resulting in greater affinity and specificity compared to single epitope immunoglobulin domains. See, e.g., Silverman et al., Nature Biotechnology. 23:1556-1561, 2005; U.S. Pat. No. 7,166, 697; and U.S. Application Nos. 2004/0175756, 2005/0048512, 2005/0053973, 2005/0089932 and 2005/0221384.

Also included are designed ankyrin repeat proteins (DARPins), which include a class of non-immunoglobulin proteins that can offer advantages over antibodies for target binding in drug discovery and drug development. Among other uses, DARPins are ideally suited for in vivo imaging or delivery of toxins or other therapeutic payloads because of their favorable molecular properties, including small size and high stability. The low-cost production in bacteria and the rapid generation of many target-specific DARPins make the DARPin approach useful for drug discovery. Additionally, DARPins can be easily generated in multispecific formats, offering the potential to target an effector DARPin to a specific organ or to target multiple polypeptides/nucleic acids with one molecule composed of several DARPins. See, e.g., Stumpp et al., Curr Opin Drug Discov Devel. 10:153-159, 2007; U.S. Application No. 2009/0082274; and PCT/EP2001/10454.

Certain embodiments include "monobodies," which typically utilize the 10th fibronectin type III domain of human fibronectin (FNfn10) as a scaffold to display multiple surface loops for target binding. FNfn10 is a small (94 residues) protein with a β-sandwich structure similar to the immunoglobulin fold. It is highly stable without disulfide bonds or metal ions, and it can be expressed in the correctly folded form at a high level in bacteria. The FNfn10 scaffold is compatible with virtually any display technologies. See, e.g., Batori et al., Protein Eng. 15:1015-20, 2002; and Wojcik et al., Nat Struct Mol Biol., 2010; and U.S. Pat. No. 6,673,901.

Anticalins refer to a class of antibody mimetics, which are typically synthesized from human lipocalins, a family of binding proteins with a hypervariable loop region supported by a structurally rigid framework. See, e.g., U.S. Application No. 2006/0058510. Anticalins typically have a size of about 20 kDa. Anticalins can be characterized by a barrel structure formed by eight antiparallel β-strands (a stable β-barrel scaffold) that are pairwise connected by four peptide loops and an attached α-helix. In certain aspects, conformational deviations to achieve specific binding are made in the hypervariable loop region(s). See, e.g., Skerra, FEBS J. 275:2677-83, 2008, herein incorporated by reference.

The therapeutic agents, e.g. binding agents, described herein which inhibit the binding of a KLF transcription factor to its endogenous transcription factor binding site(s), can be used in any of the methods and compositions described herein.

Methods for Use

Embodiments of the present invention include methods of using therapeutic agents described herein (e.g., oligonucleotide decoys, binding agents), which inhibit or otherwise reduce binding of one or more KLF transcription factors to its endogenous transcription binding site, and related compositions, to modulate the activity of one or more KLF transcription factors. In particular embodiments, the one or more transcription factors is selected from the group consisting of KLF1, KLF2, KLF3, KLF4, KLF5, KLF6, KLF8, KLF9, KLF10, KLF11, KLF12, KLF13, KLF14, KLF15, KLF16 and KLF17.

The methods can be used, for example, to treat pain in a subject, to modulate transcription of a gene present in a cell involved in nociceptive signaling, to modulate transcription of a gene present in a cell involved in perception of pain in a subject, and/or to modulate nociceptive signaling in a cell, for example, in a subject. Such methods can be practiced in vitro, for instance, by contacting a cell with a therapeutic agent (e.g., oligonucleotide decoy) or related composition, or in vivo, for instance, by administering to a subject in need thereof a therapeutic agent (e.g., oligonucleotide decoy) or related composition. In particular embodiments, the therapeutic agent is an oligonucleotide decoy or population of oligonucleotide decoys, as described herein.

Thus, certain embodiments include methods for treating pain in a subject, comprising administering to the subject a therapeutically effective amount of a therapeutic agent, wherein the therapeutic agent inhibits binding of a transcription factor to its transcription binding site, and wherein the transcription factor is selected from the group consisting of KLF1, KLF2, KLF3, KLF4, KLF5, KLF6, KLF8, KLF9, KLF10, KLF11, KLF12, KLF13, KLF14, KLF15, KLF16 and KLF17. Also included are methods of treating pain in a subject in need thereof, comprising administering to the subject a therapeutically effective amount of one or more oligonucleotide decoys described herein. In some embodiments, methods of preventing pain in a subject are provided, for example, prophylactic methods of treating or managing pain. Such methods comprise administering to a subject in need thereof (e.g., a patient likely to develop pain, e.g., post-operative pain) a therapeutically effective amount of an oligonucleotide decoy described herein.

Thus, in certain embodiments, an oligonucleotide decoy and/or pharmaceutical composition comprising the same is administered to a subject in need thereof, for example, such as an animal (e.g., a bird, mammal, primate, human patient), suffering from or expected to suffer from pain. Particular examples of pain include, but are not limited to, mechanical pain (e.g., mechanical hyperalgesia and/or allodynia), chemical pain, temperature pain, chronic pain, sub-chronic pain, acute pain, sub-acute pain, inflammatory pain, neuropathic pain, muscular pain, skeletal pain, post-surgery pain, radicular pain, back pain, arthritis pain, and/or diabetes pain. In certain embodiments, the oligonucleotide decoys and/or pharmaceutical compositions thereof are administered to a patient, such as an animal, as a preventative measure against pain including, but not limited to, any one or more of the foregoing examples of pain. In some embodiments, the pain is post-operative pain, chronic pain, inflammatory pain, neuropathic pain, muscular pain, and/or skeletal pain. In certain embodiments, the oligonucleotide decoys and/or pharmaceutical compositions thereof may be used for the prevention of one facet of pain while concurrently treating another symptom of pain.

In particular embodiments, the pain is chronic pain. In some embodiments, the pain is neuropathic pain, for example, chronic neuropathic pain and/or (chronic) neuropathic pain that is associated with inflammation (e.g., neuro-inflammation). In certain embodiments, the pain is associated with inflammation, for example, chronic pain associated with inflammation, chronic neuropathic pain associated with inflammation. In some embodiments, the pain is associated with the central nervous system and/or a visceral disorder. In some embodiments, the pain is post-surgical pain.

In some embodiments, the therapeutic agent (e.g., oligonucleotide decoy, population of oligonucleotide decoys, binding agent) or composition that is administered to treat, manage, and/or prevent pain provides a binding ratio of KLF15/KLF9 equal to or less than about 0.8 or equal to or higher than about 1.0 based on $OD_{450}$ values (or equivalent standard ELISA measurement units) in a standard ELISA assay (see supra). In specific embodiments, the foregoing is used in the treatment of neuropathic pain.

In particular embodiments, the therapeutic agent (e.g., oligonucleotide decoy, population of oligonucleotide decoys, binding agent) or composition that is administered to treat, manage, and/or prevent pain provides a total transcription factor binding capacity to KLF6 and KLF9 that is equal to or higher than a predetermined amount, for instance, an optical density value of about 0.2 $OD_{450}$ (or comparable binding level using equivalent standard ELISA measurement units) in a standard ELISA assay (see supra). In some embodiments, the total transcription factor binding capacity to KLF6 and KLF9 (as indicated by 1/(KLF6+ KLF9)) is equal to or less than about 5, 4, 3, 2, 1, 0.5, 0.1, or less (including all ranges and integers in between) based on $OD_{450}$ values (or an equivalent standard ELISA measurement unit, e.g., fluorescence) from a standard ELISA assay. In specific embodiments, the foregoing is used in the treatment of pain or neuropathic pain associated with inflammation Also included are methods for modulating transcription of a gene present in a cell involved in nociceptive signaling and/or the perception of pain in a subject, comprising administering to the cell a therapeutically effective amount of a therapeutic agent, wherein the therapeutic agent inhibits binding of a transcription factor to its transcription factor binding site, wherein the transcription factor is selected from the group consisting of KLF1, KLF2, KLF3, KLF4, KLF5, KLF6, KLF8, KLF9, KLF10, KLF11, KLF12, KLF13, KLF14, KLF15, KLF16 and KLF17. In some embodiments, the therapeutic agent includes one or more oligonucleotide decoys described herein. In certain embodiments, modulation of transcription comprises suppressing or repressing gene expression. In some embodiments, modulation of transcription comprises stabilizing gene expression. In particular embodiments, modulation of transcription comprises activating or inducing gene expression. In certain embodiments, the gene is involved in nociceptive signaling. Genes involved in nociceptive signaling include, but are not limited to, genes encoding membrane proteins (e.g., ion channels, membrane receptors, etc.), soluble signaling molecules (e.g., intracellular signaling molecules or neurotransmitters), synthetic enzymes (e.g., neurotransmitter synthesis enzymes), and transcription factors. Specific examples of such proteins include, but are not limited to, BDNF (regulated by KLF9), TGFB1 (regulated by KLF6), CDKN1A, JUN, GFAP (regulated by KLF15); and others such as BDKRB2, HTR3A, SCN9A, GRM5, NOS1, GCH1, CDK5R1, CACNA1B, P2XR3 and PNMT.

Some embodiments include methods for modulating nociceptive signaling in a cell, comprising administering to the cell a therapeutically effective amount of a therapeutic agent, wherein the therapeutic agent inhibits binding of a transcription factor to its transcription factor binding site, wherein the transcription factor is selected from the group consisting of KLF1, KLF2, KLF3, KLF4, KLF5, KLF6, KLF8, KLF9, KLF10, KLF11, KLF12, KLF13, KLF14, KLF15, KLF16 and KLF17. In some embodiments, the therapeutic agent includes one or more oligonucleotide decoys described herein. In certain embodiments, modulation of nociceptive signaling comprises suppressing or repressing nociceptive signaling. In some embodiments, modulation of nociceptive signaling comprises activation of an inhibitor of nociceptive signaling. In particular embodiments, modulation of nociceptive signaling comprises increasing proteolytic degradation of a protein involved in nociceptive signaling in a cell. In certain embodiments, modulation of protein degradation comprises stimulating proteasome function. In certain embodiments, the protein is involved in nociceptive signaling. Proteins involved in nociceptive signaling include, but are not limited to membrane proteins (e.g., ion channels, membrane receptors, etc.), soluble signaling molecules (e.g., intracellular signaling molecules or neurotransmitters), synthetic enzymes (e.g., neurotransmitter synthesis enzymes), and transcription factors. Specific examples of such proteins include, but are not limited to, BDNF (regulated by KLF9), TGFB1 (regulated by KLF6), CDKN1A, JUN, GFAP (regulated by KLF15); and others such as BDKRB2, HTR3A, SCN9A, GRM5, NOS1, GCH1, CDK5R1, CACNA1B, P2XR3 and PNMT.

In certain embodiments, the cell of the various methods is provided in vivo (e.g., in a subject suffering from pain or likely to suffer from pain). A cell provided in vivo can be located in different locations including, but not limited to, a dorsal root ganglia and/or the spinal cord. In other embodiments, the cell of the various methods is provided in vitro (e.g., in a petri dish). The cell can be any cell involved in nociceptive signaling, including, but not limited to, a neuron (e.g., a pain neuron from dorsal root ganglia and/or the spinal cord or from the sympathetic nervous system), a glial cell, a tissue supportive cell (e.g., fibroblast), an immune cell, or a cell from a cell line (e.g., a PC12 cell).

In some embodiments, the oligonucleotide decoys and/or pharmaceutical compositions thereof are used in combination therapy with at least one other therapeutic agent. Examples of other therapeutic agents include but are not limited to one or more additional oligonucleotide decoys. The oligonucleotide decoy and/or pharmaceutical composition thereof and the therapeutic agent can act additively or, more preferably, synergistically. In some embodiments, an oligonucleotide decoy and/or a pharmaceutical composition thereof is administered concurrently with the administration of another therapeutic agent, including another oligonucleotide decoy. In other embodiments, an oligonucleotide decoy or a pharmaceutical composition thereof is administered prior or subsequent to administration of another therapeutic agent, including another oligonucleotide decoy.

For administration to a subject in need thereof, the oligonucleotide decoys and/or pharmaceutical compositions described herein may be administered by any convenient route. Particular examples include administration by infusion or bolus injection, by absorption through epithelial or mucocutaneous linings (e.g., oral mucosa, rectal and intestinal mucosa, etc.), and by oral administration. Administration can be systemic or local. Various delivery systems are known in the art, including, e.g., encapsulation in liposomes, microparticles, microcapsules, capsules, etc., which can be used to administer a compound and/or pharmaceutical composition thereof. Methods of administration include, but are not limited to, intradermal, intramuscular, intraperitoneal, intravenous, subcutaneous, intranasal, epidural/peridural, oral, sublingual, intranasal, intracerebral, intravaginal, transdermal, rectally, by inhalation or topically, particularly to the ears, nose, eyes, or skin. In certain embodiments, the oligonucleotide decoy is administered perineurally, epidurally/peridurally, intrathecally, or intradermally. In certain embodiments, more than one oligonucleotide decoy is administered to a patient. The preferred mode of administration is left to the discretion of the practitioner, and will depend in-part upon the site of the medical condition.

In specific embodiments, it may be desirable to administer one or more oligonucleotide decoys locally to the area in need of treatment. This may be achieved, for example, and not by way of limitation, by local infusion during surgery, topical application (e.g., in conjunction with a wound dressing after surgery), by injection, by means of a catheter, by means of a suppository, or by means of an implant, said implant being of a porous, non-porous, or gelatinous material, including membranes, such as sialastic membranes, or fibers. In some embodiments, administration can be by direct injection at the site (e.g., former, current, or expected site) of pain.

In certain embodiments, it may be desirable to introduce one or more oligonucleotide decoys into the nervous system by any suitable route, including but not restricted to intraventricular, intrathecal, perineural and/or epidural/peridural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

The amount of oligonucleotide decoy that will be effective in the treatment or prevention of pain in a patient will depend on the specific nature of the condition and can be determined by standard clinical techniques known in the art. In addition, in vitro or in vivo assays may optionally be employed to help identify optimal dosage ranges. The amount of a oligonucleotide decoy administered will, of course, be dependent on, among other factors, the subject being treated, the weight of the subject, the severity of the affliction, the manner of administration, and the judgment of the prescribing physician. In certain embodiments, a single dose of oligonucleotide decoy comprises about 5 μg to about 15 mg, about 50 μg to about 7.5 mg, about 100 μg to about 1 mg, about 250 μg to about 750 μg, or about 500 μg of oligonucleotide decoy per kilogram (kg) of body weight.

In some embodiments, the dosage forms are adapted to be administered to a patient no more than twice per day, more preferably, only once per day. Dosing may be provided alone or in combination with other drugs and may continue as long as required for effective treatment or prevention of pain.

Compositions and Kits

Certain embodiments include compositions, for example, pharmaceutical or therapeutic compositions, comprising one or more therapeutic agents (e.g., oligonucleotide decoys, binding agents) described herein, optionally in combination with one or more pharmaceutically-acceptable carriers (e.g., pharmaceutical-grade carriers).

The pharmaceutical compositions disclosed herein comprise a therapeutically effective amount of one or more therapeutic agents (e.g., oligonucleotide decoys), preferably, in purified form, together with a suitable amount of a pharmaceutically-acceptable carrier, so as to provide a form for proper administration to a patient. When administered to a patient, therapeutic agents such as oligonucleotide decoys and pharmaceutically-acceptable carriers are preferably sterile. Examples of pharmaceutically-acceptable carriers include, but are not limited to, saline, phosphate buffered saline (PBS), tris buffer, water, aqueous ethanol, emulsions, such as oil/water emulsions or triglyceride emulsions, tablets and capsules. Water is a preferred vehicle when oligonucleotide decoys are administered intravenously. Saline solutions and aqueous dextrose and glycerol solutions can also be employed as liquid vehicles, particularly for injectable solutions. Suitable pharmaceutically-acceptable carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds disclosed herein into preparations which can be used pharmaceutically. Proper formulation is dependent upon the route of administration chosen.

Pharmaceutical compositions can take the form of solutions, suspensions, emulsions, tablets, pills, pellets, capsules, capsules containing liquids, powders, sustained-release formulations, suppositories, aerosols, sprays, suspensions, or any other form suitable for use. Other examples of suitable pharmaceutical vehicles have been described in the art (see Remington's Pharmaceutical Sciences, Philadelphia College of Pharmacy and Science, 19th Edition, 1995).

Pharmaceutical compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol), oils, alcohols, slightly acidic buffers between pH 4 and pH 6 (e.g., acetate, citrate, or ascorbate at between about 5 mM to about 50 mM), etc. Additionally, flavoring agents, preservatives, coloring agents, bile salts, acylcarnitines and the like may be added.

For buccal administration, the compositions may take the form of tablets, lozenges, etc., formulated in conventional manner. Liquid drug formulations suitable for use with nebulizers and liquid spray devices and EHD aerosol devices will typically include a compound with a pharmaceutically acceptable vehicle. In some aspects, the pharmaceutically acceptable vehicle is a liquid such as alcohol, water, polyethylene glycol or a perfluorocarbon. Optionally, another material may be added to alter the aerosol properties of the solution or suspension of compounds. In some aspects, the material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound may also be formulated in rectal or vaginal compositions such as suppositories or retention enemas, e.g., containing conventional suppository bases such as cocoa butter or other glycerides. In addition to the formulations described previously, a compound may also be formulated as a depot preparation. Such long acting formulations may be administered by implantation (for example, subcutaneously or intramuscularly) or by intramuscular injection. Thus, for example, a compound may be formulated with suitable polymeric or hydrophobic materials (for example, as an emulsion in an acceptable oil) or ion exchange resins, or as sparingly soluble derivatives, for example, as a sparingly soluble salt.

An oligonucleotide decoy may be included in any of the herein-described formulations, or in any other suitable formulation, as a pharmaceutically acceptable salt, a solvate or hydrate. Pharmaceutically acceptable salts substantially retain the activity of the parent compound and may be prepared by reaction with appropriate bases or acids and tend to be more soluble in aqueous and other protic solvents than the corresponding parent form.

In some instances, liposomes may be employed to facilitate uptake of the oligonucleotide decoys into cells, for example, in vitro or in a subject (see, e.g., Williams, S. A., Leukemia 10(12):1980-1989, 1996; Lappalainen et al., Antiviral Res. 23:119, 1994; Uhlmann et al., Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for oligonucleotide decoy administration, for example, as described in WO 93/01286. Alternatively, the oligonucleotide decoys may be administered in microspheres or microparticles. (See, e.g., Wu, G. Y. and Wu, C. H., J. Biol. Chem. 262:4429-4432, 30 1987). Alternatively, the use of gas-filled microbubbles complexed with the oligonucleotide decoys can enhance delivery to target tissues, as described in U.S. Pat. No. 6,245,747. Sustained release compositions may also be used. These may include semipermeable polymeric matrices in the form of shaped articles such as films or microcapsules.

Oligonucleotide decoys can be introduced into cells using art-recognized techniques (e.g., transfection, electroporation, fusion, liposomes, colloidal polymeric particles and viral and non-viral vectors as well as other means known in the art). The method of delivery selected will depend at least on the oligonucleotide chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, oligonucleotide decoys may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (see, e. g., Dokka and Rojanasakul, Advanced Drug Delivery Reviews 44:35-49, incorporated by reference in its entirety).

In certain embodiments, one or more oligonucleotide decoys are provided in a kit. In certain embodiments, the kit includes an instruction, e.g., for using said one or more oligonucleotide decoys. In certain embodiments, said instruction describes one or more of the methods of the present invention, e.g., a method for preventing or treating pain, a method of modulating gene expression in a cell, a method for modulating nociceptive signaling in a cell, a method for modulating protein degradation in a cell, etc. In certain embodiments, the oligonucleotide decoys provided in a kit are provided in lyophilized form. In certain related embodiments, a kit that comprises one or more lyophilized oligonucleotide decoys further comprises a solution (e.g., a pharmaceutically-acceptable saline solution) that can be used to resuspend one or more of the oligonucleotide decoys.

The following examples are intended to illustrate but not to limit the invention. Each of the patent and non-patent references referred to herein is incorporated by reference in its entirety.

EXAMPLES

Example 1

Targeting the KLF Family for the Treatment of Pain

Oligonucleotide decoys targeted against members of the Krüppel-like family of transcription factors (KLFs) were designed, characterized for KLF-binding, and tested in animal models of neuropathic and neuro-inflammatory pain.

Cross-analysis of the KLF binding patterns, efficacy amplitude, and duration across two separate neuropathic and neuro-inflammatory pain models (described below) showed that the oligonucleotide decoys TFD16 (GATCCTTTGCCTCCTTCGATCCTTTGCCTCCTTCAAG; SEQ ID NO:37) and TFD17 (GGTGTTTGGGAGAGCTTTGGGAGGATACG; SEQ ID NO:38) were effective in both models and acted through inhibiting KLF6, 9 and/or 15 (data not shown). These data showed that efficacy for reducing chronic neuropathic pain is effective through the combined inhibition of KLF9 and KLF15, and efficacy for reducing chronic neuro-inflammatory pain is effective through the combined inhibition of KLF6 and KLF9.

Consequently, TFD16 and TFD17 were selected as sequence matrices to generate additional oligonucleotide decoy sequences with complementary KLF6, 9, and 15 binding patterns. Based on this analysis, the oligonucleotide decoys in Table 2 (supra) were prepared tested for KLF binding, and those in Table E1 (below) were further tested in animal models of pain, as described below.

TABLE E1

| Name | Sequence (5' to 3') | SEQ ID NO: |
|---|---|---|
| 16.6.2 | CCTTTGCCTCCTTCGCCTCCTTCAA | 25 |
| 16.6.5 | ATCCTTCGCCTCCTTCAA | 28 |
| 16.9 | ATCCTTTGCCTTTGCCTCCTTCAA | 12 |
| 17.1 | GCTTTGGGAGGATAC | 15 |
| 17.5 | TGTTTGGGAGAATCCTCCCAAAGC | 19 |
| 17.9 | TGTTTGGGAGAGGGAGGATAC | 23 |
| TFD3 | GCGCACCCCAGCCTGGCTCACCCACGCG | 36 |
| TFD16 | GATCCTTTGCCTCCTTCGATCCTTTGCCTCCTTCAAG | 37 |
| TFD17 | GGTGTTTGGGAGAGCTTTGGGAGGATACG | 38 |

ELISA Assay. KLF binding of the oligonucleotide decoys was measured using a customized version of an SP1 commercial ELISA kit (SP1 ELISA Kit, catalogue number EK-1090, Affymetrix). Briefly, biotin-decoy probes (12.8 pmoles/well) were incubated with 15 µg of nuclear protein extracts containing KLF transcription factors from either (a) HELA cells: for KLF1-6, 8-14, and 16-17 detection (catalogue #36010, Active motif, CA) or (b) HEK290: for KLF15 detection (catalogue #36033, Active motif, CA). For KLF 7 detection, 0.5 and 1 µg of a recombinant human KLF7 protein was utilized (Novus, CA, catalogue # NBP2-23176).

The processing of the decoy probe-protein mix was performed according to the ELISA kit supplier: the mix was loaded on streptavidin-coated 96-well plates, and the quantity of captured KLF measured with an antibody-based colorimetric detection (anti-rabbit secondary antibody conjugated to HRP) in a microplate reader ($OD_{450}$ nm). When increasing concentration of competing, non-biotinylated decoys were added to the binding mix reaction, a reduction of transcription factor binding to the biotinylated probe is a demonstration of binding specificity. All data were corrected against background signal measured internally for each ELISA run, and all testing steps and testing conditions were standardized according to the kit supplier's recommendation, including detection time with the detection buffer (i.e., 5.2 min determined as optimal for this assay), to ensure appropriate comparison of brute $OD_{450}$ binding values between ELISA runs.

For the ELISA assays, single strands of each decoy were manufactured by Invitrogen (CA), re-suspended in 100 µM stock solution in TE pH 8, NaCl 50 µM, and annealed in 4

μM working solutions as follow: (a) decoy mix (100 μL): 4 μL sense strand (100 μM)+4 μl antisense strand (100 μM)+ 89.5 μl TE pH 8+2.5 μl NaCl (1.94 M); (b) annealing: 7 min at 95° followed by slow cooling at RT for 1 h before use or storage at −20° C.

Binding specificity was assessed by measuring binding signal linearity, reduction of binding with free competitor KLF decoy, and by the lack of KLF binding to mutant decoys (See Table E2 below).

TABLE E2

Mutant decoys

| Name | Sequence (5' to 3') | SEQ ID NO: |
|---|---|---|
| MUT1 S | ATGCAGGAGAAAGATTGGCGTAGTATCTACTAG | 39 |
| MUT1 AS | CTTCATGATTTTATTGCTTTCAAAATCCAAAAT | 40 |
| MUT2 S | GTTATGCGTTTGTAGATGCTTTCGTTATAG | 41 |
| MUT2 AS | CTATTTCGAAACGATCTACATTGGCATAAC | 42 |

Rabbit primary KLF antibodies were obtained from commercially-available sources, and the secondary anti-rabbit antibody conjugated to HRP used for the KLF assay was the antibody provided in the ELISA kit (dilution 1:200).

In vivo Efficacy Studies. The materials and methods for the animal models of pain are described below.

Animals. Sprague-Dawley rats, 250-300 g, males, Harlan Industries (Livermore, Calif.).

Test and control articles. For animal testing, oligonucleotide decoys were manufactured by Trilink Biotechnologies (CA) and formulated as 10 mM or 15 mM stock solutions (Tris-pH 7.5, CaCl2). Each decoy was prepared for 20 μL injections at the appropriate concentration for the selected dose delivery. Oligonucleotide decoy and vehicle controls (Tris-10 mM, 140 mM NaCl, pH 7.5) were provided to the testing site in a blinded fashion and in ready-to-use vials.

Spared Nerve Injury (SNI) Model. Anaesthesia was induced with 2% isoflurane in $O_2$ at 2 L/min and maintained with 0.5% isofluorane in $O_2$. Rats were then shaved and aseptically prepared for surgeries. Spared nerve injury was done based on the method described by Decosterd et al (Decosterd and Woolf, 2000). Briefly, skin and fascia of left thigh were incised, two heads of m. biceps femoris spread, and 3 terminal branches of sciatic nerve exposed. Tibial and comon peroneal were tightly ligated, dissected distally to ligation, and 2-3 mm of nerve trunk was removed. The sural branch was left intact. The wound was closed in a layered fashion.

Chronic Constriction Injury (CCI) Model. Following the Chronic Constriction Injury model (Bennett and Xie, 1988), the right common sciatic nerve was exposed at the level of the middle of the thigh by blunt dissection through the biceps femoris. Proximal to the sciatic's trifurcation, about 12 mm of nerve was freed of adhering tissue and four ligatures were tied loosely around it with about 1 mm spacing. The length of nerve thus affected was ~6-8 mm long. Care was taken to tie the ligatures such that the diameter of the nerve was seen to be just barely constricted when viewed with 40× magnification. The desired degree of constriction retarded, but did not arrest, circulation through the superficial epineural vasculature and sometimes produced a small, brief twitch in the muscle surrounding the exposure. The incision was closed in layers.

Mechanical Hypersensitivity. Pain was measured as mechanical hypersensitivity using repetitive von Frey filament testing. Briefly, von Frey filaments (1-4-6-8-10-10-26 g) were used to test for the responsiveness to mechanical stimulation of the hind paw. Animals were habituated on a mesh floor 1 hour prior to testing and five applications of each filament was applied. For each application, the hair was pressed perpendicularly against the paw with sufficient force to cause slight bending, and held for approximately 1-2 seconds. A positive response was noted if the paw was sharply withdrawn. Flinching immediately upon removal of the hair was also considered a positive response. Stimuli were presented successively following the pattern described above. Animals were tested at baseline just prior to surgery and at determined time-points pre- and post-injections.

Blinding & Randomization. All experiments were performed blinded. The testing sites received blinded vials and the blinding code being was broken after testing was completed.

Randomization was performed on POD14 after the baseline pain testing and before the dosing. For each tested cohort, animals were distributed in groups of 2 to 3 rats so mean POD14 von Frey values were as close as possible across the testing groups, targeting within 15% of each other if the values permits. Once animals were distributed into groups, the attribution of solution treatment to groups was at the discretion of the experimenter.

Pre-defined Inclusion & Exclusion Criteria. Animals with von Frey values ≤5 at the day of the first injection (i.e., POD14) was excluded from results analysis. The von Frey value of 5 is based on internal historical data across multiple testing sites where rats can reach this value in basal condition, pre-surgery and is therefore a threshold for the absence/ presence of model-induced hypersensitivity. If the average of mechanical hypersensitivity values of vehicle-treated were reduced by 50% or more during the first week following injection, the cohort was excluded on the ground that the pain model did not perform appropriately.

Intrathecal delivery. Oligonucleotide decoys were delivered intrathecally. Sprague-Dawley rats were anesthetized with 2% isoflurane, their backs shaved and prepared with Betadine. The rat then was placed on a bottle to keep the back arched. A 17G 1/2 needle was slid rostrally along left side of the L6 vertebra level transverse process until it reached the L5 vertebra level. The needle was then inserted between L5 and L6 until the intrathecal space was reached as indicated by tail twitch. 20 μL of decoy or vehicle were then injected intrathecally (IT). Depending on the study, rats received either a single IT injection once at POD14 following surgery, or once at POD14 and once at POD17.

Statistical Analysis. Non-parametric Student T-test followed by a T-Welsh analysis for uneven variance correction was used to analyze individual time-points and data distribution comparison between experimental conditions.

Figure 1:
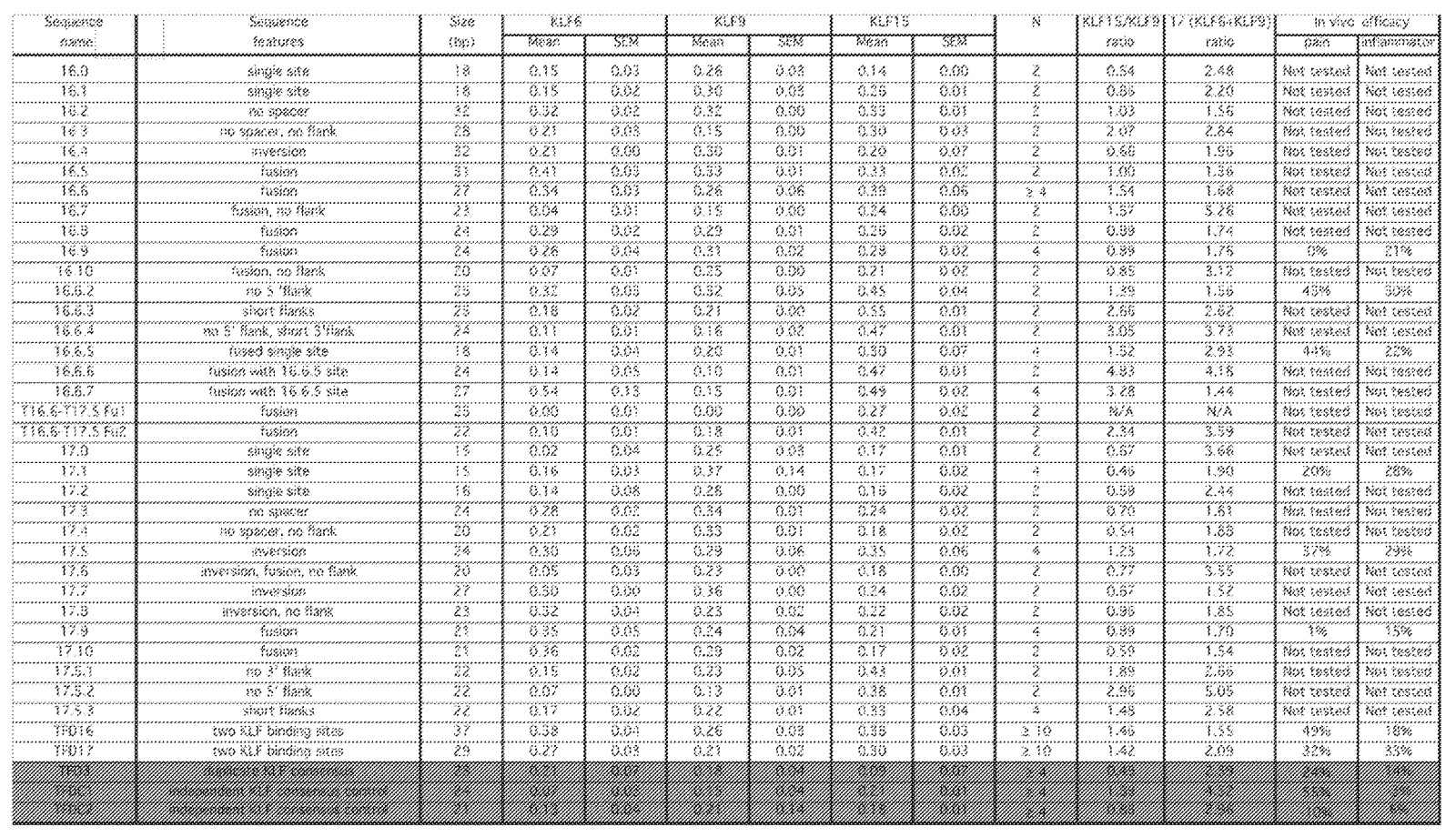

The results from the KLF-binding ELISA analysis and CCI and SNI animal models of pain with single dosing level of decoys are shown in FIGS. 1-3B. FIG. 1 shows the KLF binding characteristics of the oligonucleotide decoys from Tables 2 and E1, relative to independent control KLF decoys (highlighted in gray; see, e.g., Shields and Yang, 1998; Matsumuto et al., 1998). Binding values to KLF6, KLF9, and KLF15 are presented as mean and SEM $OD_{450}$ values from the in vitro ELISA binding assay described in Example 1. The corresponding N is also listed. The efficacy for treating neuropathic and/or neuro-inflammatory pain is presented as percentage (%) of pain reduction relative to control during the testing period of the corresponding animal studies.

Figure 2B:
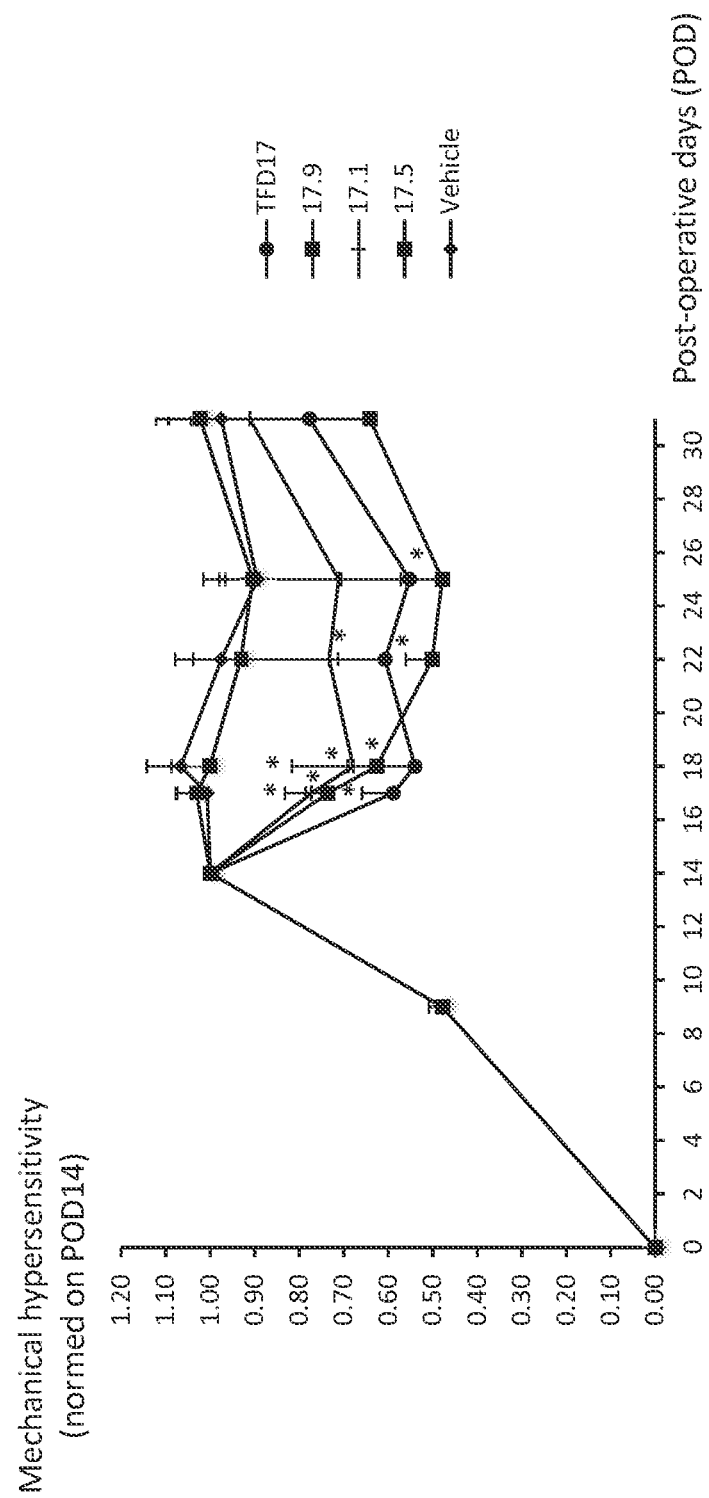
Figure 3A:
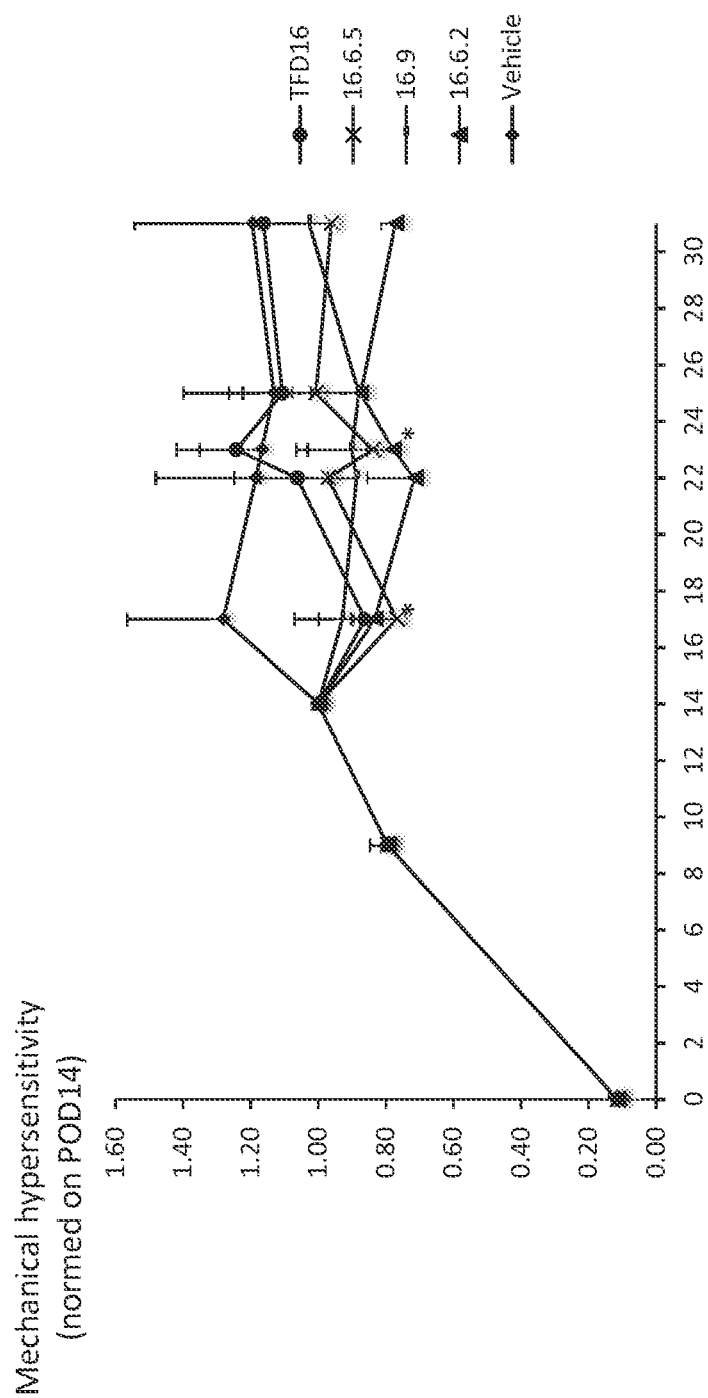
FIGS. 3A-B show the efficacy of certain of the oligonucleotide decoys in the chronic constriction injury (CCI) model of chronic neuro-inflammatory pain. Pain was measured as mechanical hypersensitivity using repetitive von Frey filaments. Oligonucleotide decoys (200 nmoles) or vehicle were injected once intrathecally at post-operative day 14 (POD14). Mean+SEM values of total responses to von Frey stimulations were normalized on the baseline pain values measured at POD14 prior to the injection of vehicle or decoys; pre-injection data before POD14 are combined across groups, T-test vs. vehicle at a given time-point: *p≤0.1, ** p≤0.05, decoy vs. vehicle data distribution post-treatment (POD 17-POD31): p=0.23 for TFD16, p=0.01 for 16.6.2, p=0.03 for 16.6.5, 0.02 for 16.9, p=0.0004 for TFD17, p=0.005 for 17.1, p=0.004 for 17.5 and p=0.12 for 17.9; n=4 rats per testing group (except 17.9: n=3 due to 1 rat exclusion due to insufficient baseline pain value at POD14). The X-axis shows post-operative days (POD).
Figure 3B:
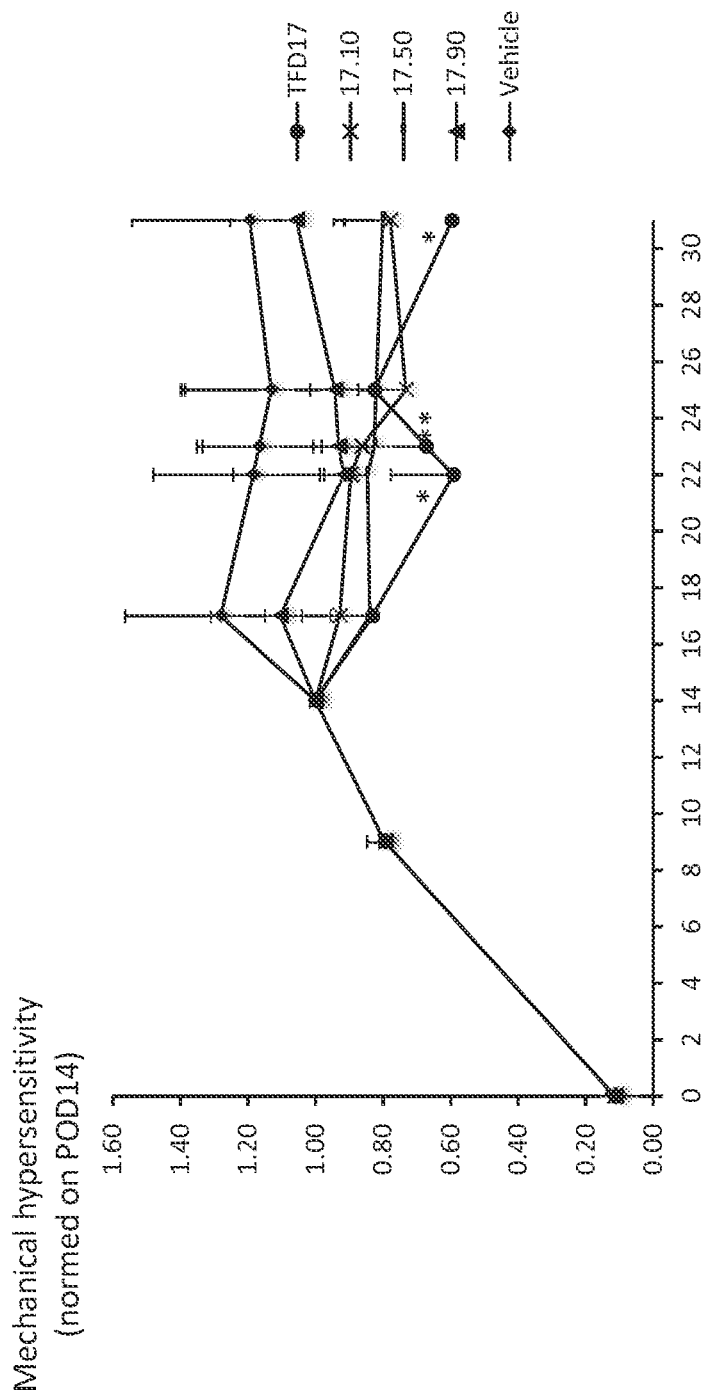

FIGS. 2A-B show the efficacy of the tested oligonucleotide decoys in the SNI model of chronic neuropathic pain, and FIGS. 3A-B show the efficacy of the tested oligonucleotide decoys in the CCI model of chronic neuro-inflammatory pain.

Figure 4C:
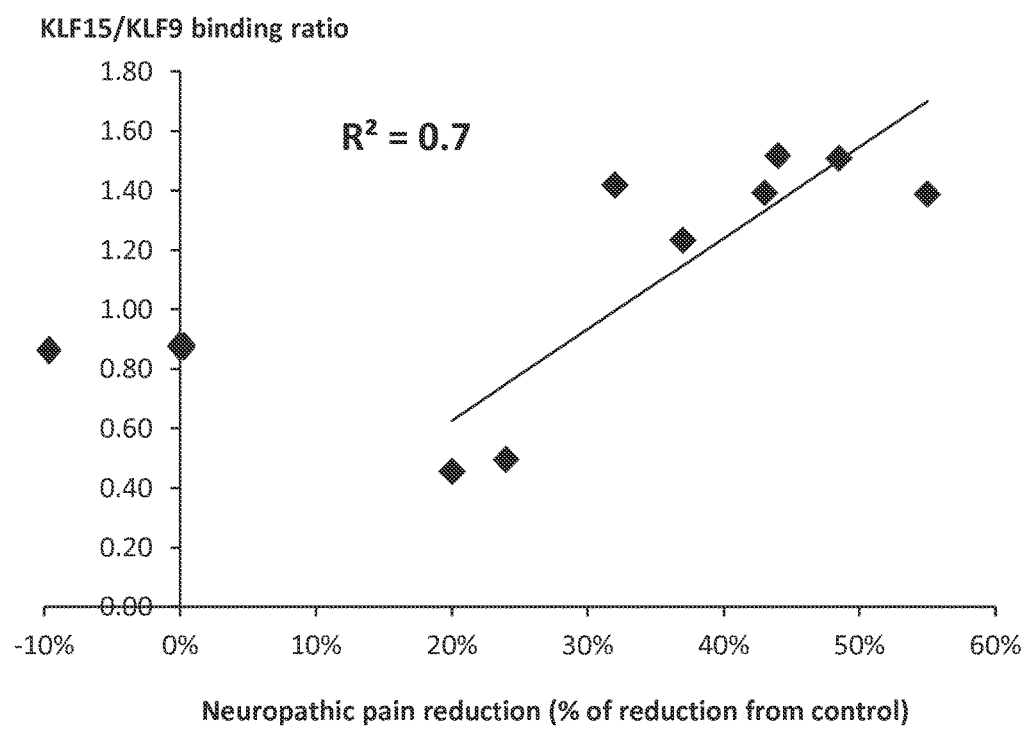

A detailed meta-analysis of the combined in vivo efficacy and in vitro binding results for all of the oligonucleotide decoys tested in vivo was conducted to characterize the relationship between the KLF binding pattern and the efficacy of the oligonucleotide decoys. FIG. 4A-C show the efficacy level of the oligonucleotide decoys for treating chronic neuropathic pain in relation to their ratio of KLF15/KLF9 binding (4A), coefficients of linear correlation between the efficacy for treating chronic neuropathic pain and the binding parameters to KLF6, KLF9 and KLF15 (4B), and a linear regression of efficacy levels in relation to KLF15/KLF9 binding ratios (4C).

Figure 5C:
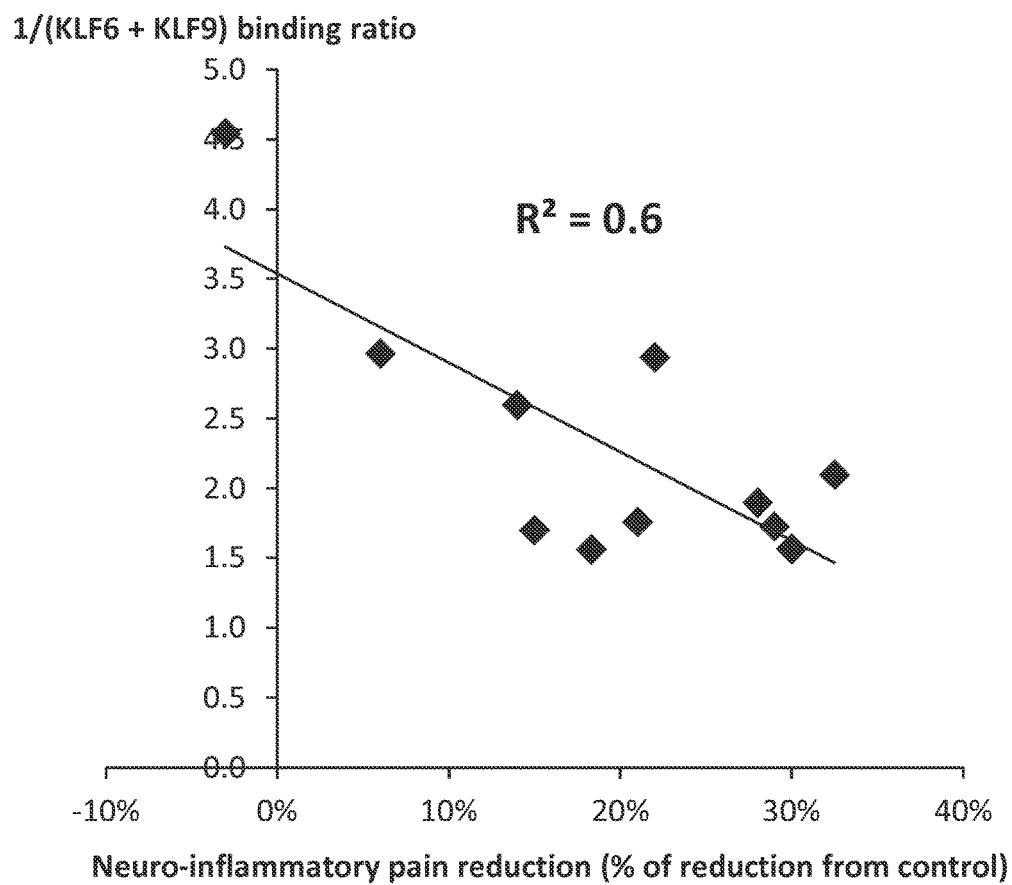

Similarly, FIGS. 5A-C show the efficacy level of the oligonucleotide decoys for treating chronic neuro-inflammatory pain in relation to their combined binding to KLF6, KLF9, and KLF15 (5A), coefficients of linear correlation between the efficacy for treating chronic neuro-inflammatory pain and the binding parameters to KLF6, KLF9 and KLF15 (5B), and a linear regression of efficacy level in relation total transcription factor binding capacity to KLF6 and KLF9, as indicated by the 1/(KLF6+KLF9) binding ratio (5C).

Figure 6:
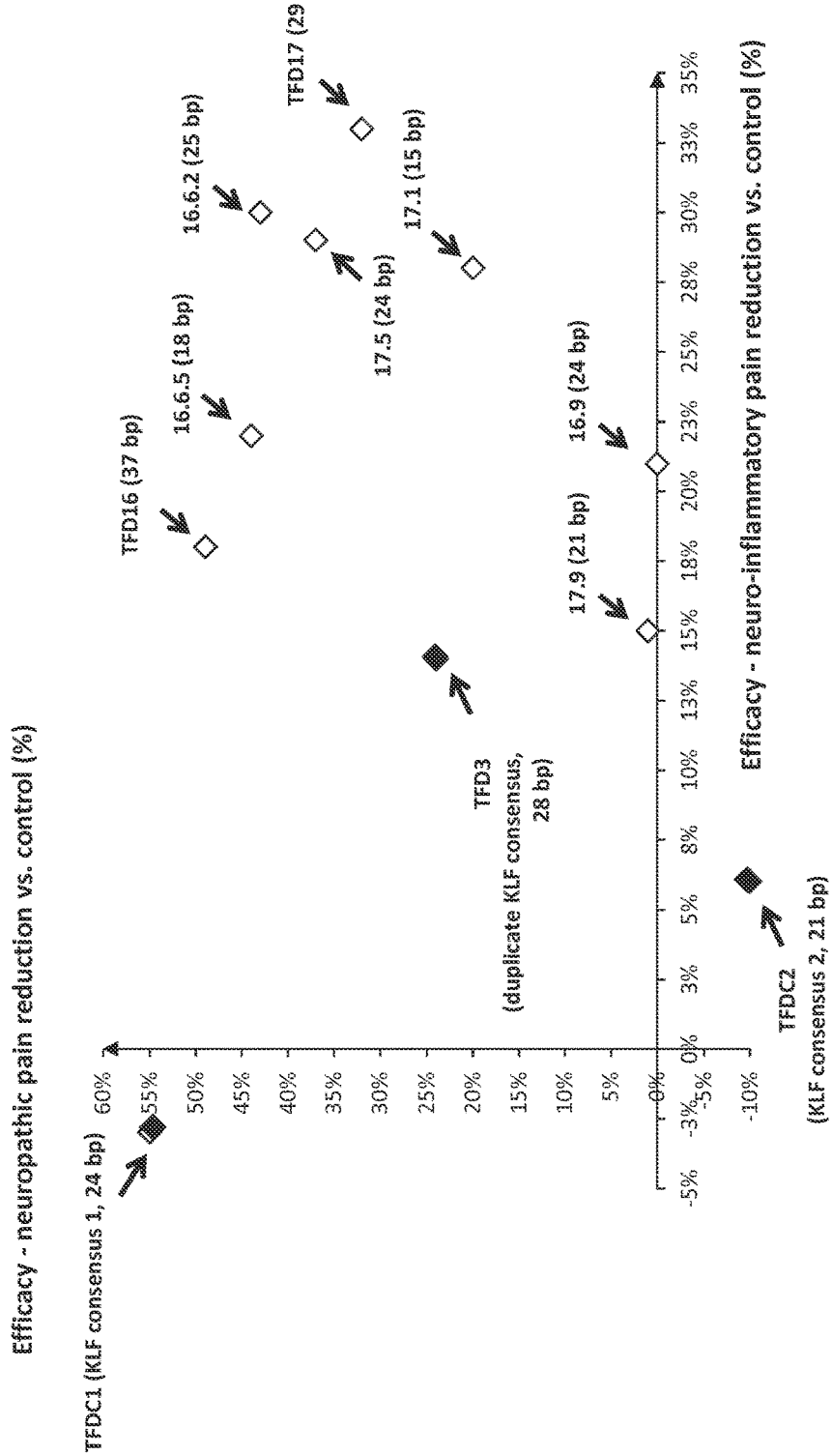
FIG. 6 shows the differential pattern of efficacy of certain of the oligonucleotide decoys (white lozenges) relative to control KLF decoys from the literature (TFDC1, TFDC2, and TFD3, which contains two KLF-consensus CACCC-box binding sites, black lozenges), across complementary etiologies of pain, from neuropathic (Y-axis) to pain including inflammatory components (X-axis).

FIG. 6 shows the differential and superior pattern of efficacy of the decoys from the invention relative to control KLF consensus decoys from the literature (TFDC1, TFDC2, and TFD3), across complementary etiologies pain, from neuropathic (Y-axis) to pain including inflammatory components (X-axis).

Figure 7:
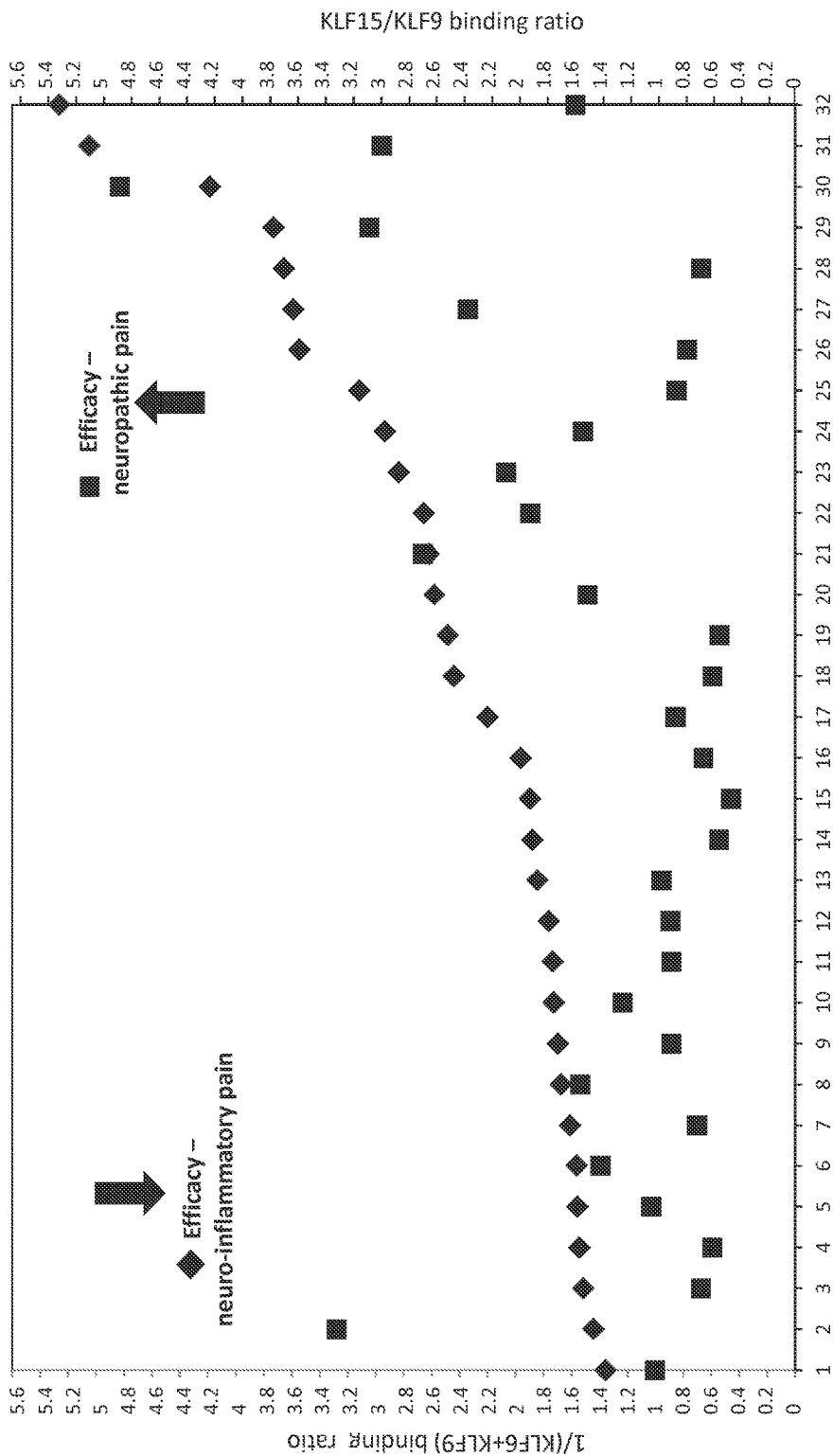
FIG. 7 shows a plot of the 1/(KLF6+KLF9) binding ratio (diamonds), which is indicative of the efficacy for treating neuro-inflammatory pain (the lower, the more efficacy), and of the KLF15/KLF9 binding ratio (squares), which is indicative of the efficacy for treating neuropathic pain (the higher, the more efficacy), for the oligonucleotide decoys of the invention in Table 2 (X-axis, KLF decoys: 1=16.5, 2=16.6.7, 3=17.7, 4=17.1, 5=16.2, 6=16.6.2, 7=17.3, 8=16.6, 9=17.9, 10=17.5, 11=16.8, 12=16.9, 13=17.8, 14=17.4, 15=17.1, 16=16.4, 17=16.1, 18=17.2, 19=16.0, 20=17.5.3, 21=16.6.3, 22=17.5.1, 23=16.3, 24=16.6.5, 25=16.10, 26=17.6, 27=T16.6-T17.5 Fu2, 28=17.0, 29=16.6.4, 30=16.6.6, 31=17.5.2, 32=16.7, T16.6-T17.5 Fu1 not listed due to non-applicable values).

FIG. 7 shows a plot of the 1/(KLF6+KLF9) binding ratio, which is indicative of the efficacy for treating neuro-inflammatory pain (the lower, the more efficacy), and the KLF15/KLF9 binding ratio, which is indicative of the efficacy for treating neuropathic pain (the higher, the more efficacy), for the oligonucleotide decoys in Table 2. Each number in the X-axis corresponds to an individual decoy.

Figure 8A:
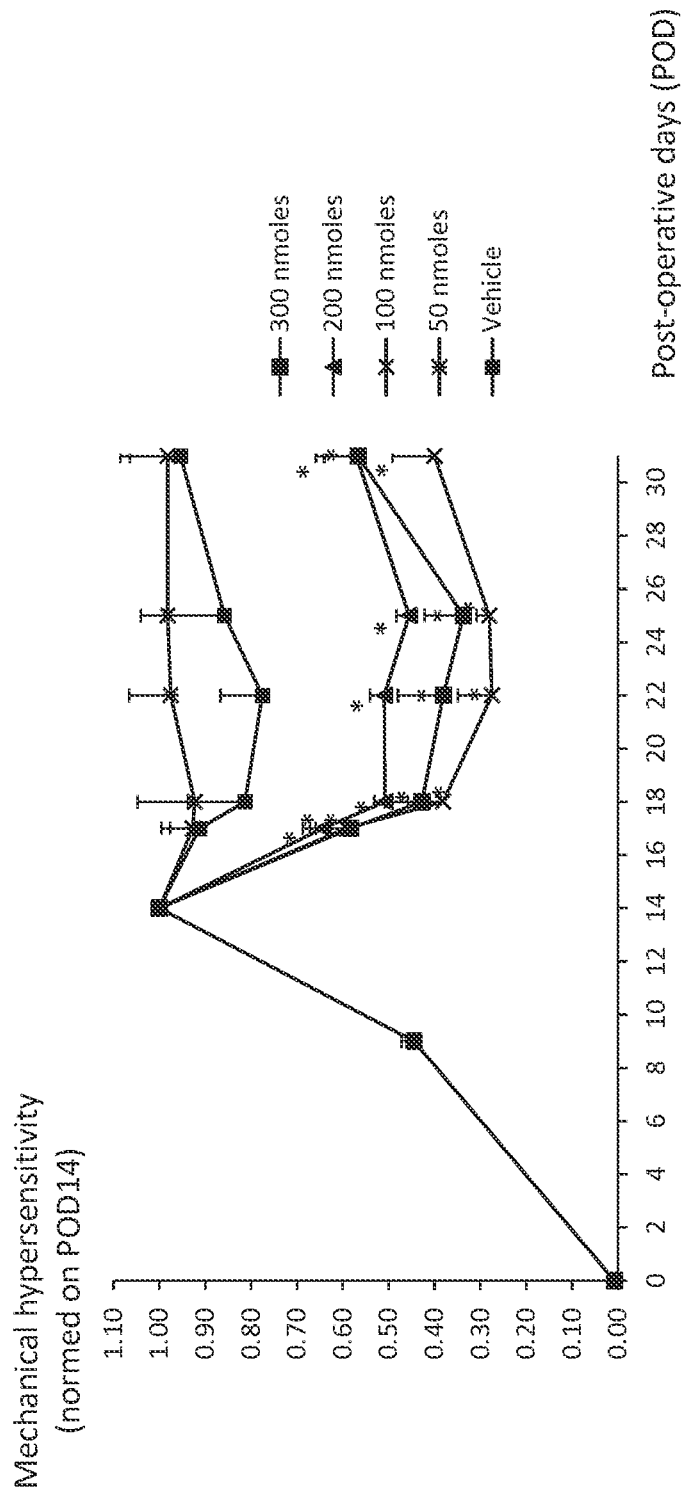
FIGS. 8A-B show the effect of ascending dose levels of 16.6.5 oligonucleotide decoy in the SNI model of chronic neuropathic pain (A) and in the CCI model of chronic neuro-inflammatory pain (B). Pain was measured as mechanical hypersensitivity using repetitive von Frey filaments. 16.6.5 or vehicle were injected once intrathecally at post-operative day 14 (POD14). Mean+SEM values of total responses to von Frey stimulations were normalized on the baseline pain values measured at POD14 prior to the injection of vehicle or decoys; pre-injection data before POD14 were combined across groups, T-test vs. vehicle at a given time point: * p≤0.05, 16.6.5 vs. vehicle data distribution post-treatment (POD 17-POD31): p≤0.001 for 100, 200 and 300 nmoles dose-levels in the SNI model, p=0.02 for 200 nmoles and p≤0.001 for 300 nmoles dose-levels in the CCI model; n=4 rats per testing group. The X-axis shows post-operative days (POD).
Figure 8B:
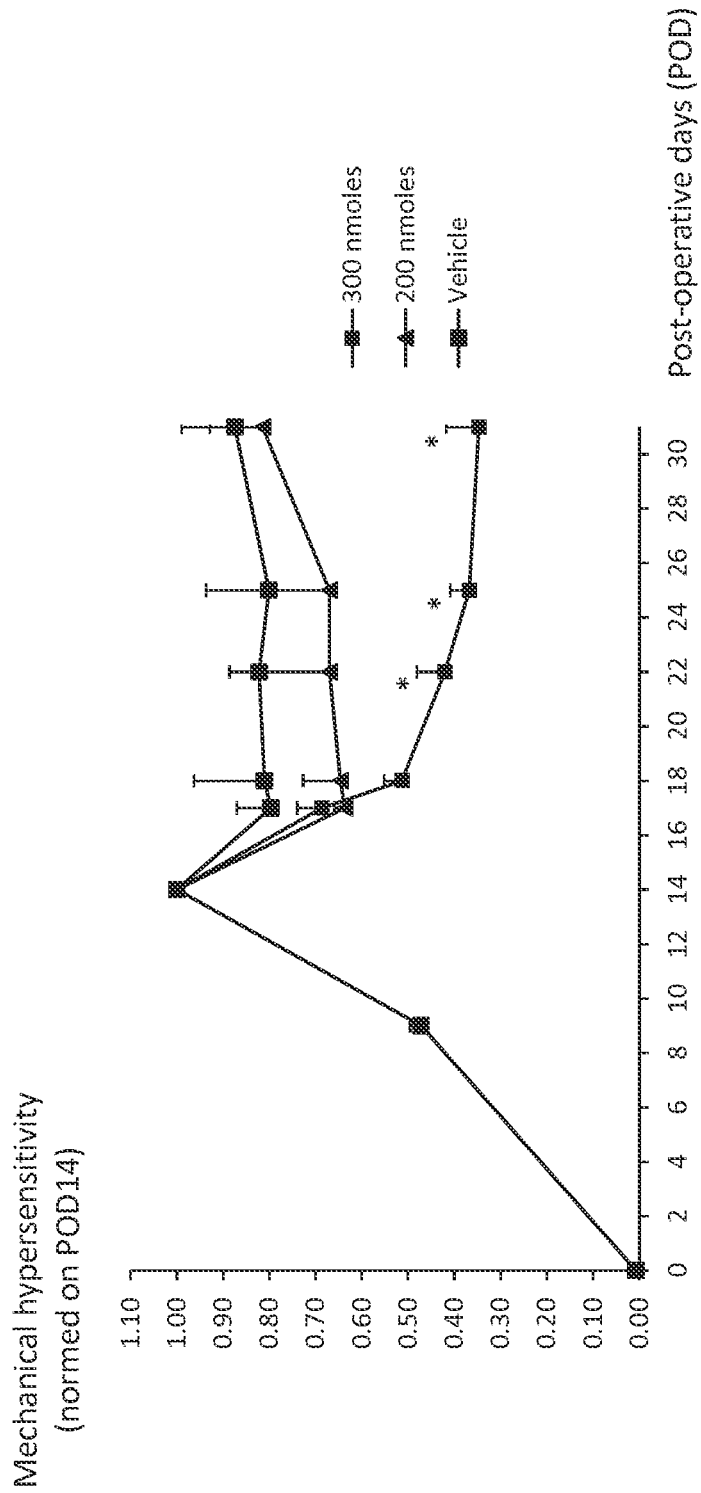

To further characterize the therapeutic profile of the 16.6.5 oligonucleotide decoy, dose response studies were performed in the SNI and CCI animal models. FIGS. 8A-B show the robust and long-lasting efficacy of ascending dose levels from 50 to 300 nmoles in these two animal models of pain.

Altogether, these studies not only identify the family of KLF transcription factors as targets of therapeutic relevance for treating pain, but also identify a set of oligonucleotide sequences with unique binding profile to KLF transcription factors, relative to previously described KLF sequences, which are associated with a unique and robust potential for treating in vivo pain across multiple etiologies.

The invention claimed is:

1. An oligonucleotide decoy comprising a combination of at least two transcription factor binding sites, wherein each transcription factor binding site binds to a transcription factor selected from the group consisting of KLF1, KLF2, KLF3, KLF4, KLF5, KLF6, KLF7, KLF8, KLF9, KLF10, KLF11, KLF12, KLF13, KLF14, KLF15, KLF16 and KLF17, wherein the decoy comprises a sequence represented by Formula 1 or Formula 2:

$$a_1t_2c_3c_4T_5T_6Y_7G_8M_9M_{10}T_{11}Y_{12}Y_{13}K_{14}Y_{15}C_{16}N_{17}H_{18}h_{19}n_{20}n_{21}v_{22}n_{23}n_{24}y_{25}m_{26}h_{27}w_{28}b_{29}v_{30}a_3 \quad \text{(Formula 1; SEQ ID NO:1)};$$

$$t_1g_2t_3k_4b_5K_6K_7D_8D_9V_{10}D_{11}N_{12}S_{13}D_{14}N_{15}B_{16}N_{17}N_{18}d_{19}V_{20}m_{21}b_{22}v_{23}m_{24}h_{25}r_{26}m_{27}a_{28} \quad \text{(Formula 2; SEQ ID NO:2)},$$

wherein S is G or C; W is A or T; Y is T or C; D is A, G, or T; B is C, G, or T; K is T or G; M is C or A; H is C, T, or A; V is C, G, or A; R is A or G; and N is any nucleotide, wherein lower case letters can be either present or absent, and wherein the numbers in subscript represent the position of a nucleotide in the sequence.

2. The oligonucleotide decoy of claim 1, wherein the oligonucleotide decoy is about 15 to about 35 base pairs in length.

3. The oligonucleotide decoy of claim 1, wherein the oligonucleotide decoy comprises a first transcription factor binding site and a second transcription factor binding site, and wherein the first and the second transcription binding sites overlap.

4. The oligonucleotide decoy of claim 1, wherein the oligonucleotide decoy has a first transcription factor binding site, a second transcription factor binding site, and a third transcription factor binding site, and wherein the first, second, and third transcription factor binding sites overlap.

5. The oligonucleotide decoy of claim 4, wherein the first transcription factor binding site binds to KLF6, the second transcription factor binding site binds to KLF9 and the third transcription factor binding site binds to KLF15.

6. The oligonucleotide decoy of claim 3, wherein the first transcription factor binding site binds to KLF9 and the second transcription factor binding site binds to KLF15.

7. The oligonucleotide decoy of claim 3, wherein the first transcription factor binding site binds to KLF9 and the second transcription factor binding site binds to KLF6.

8. A population of oligonucleotide decoys of claim 1, wherein the population of oligonucleotide decoys provides a transcription factor binding ratio of KLF15/KLF9 equal to or less than about 0.8 or equal to or higher than about 1.0 in a standard ELISA assay.

9. A population of oligonucleotide decoys of claim 1, wherein the population of oligonucleotide decoys provides a total transcription factor binding capacity to KLF6 and KLF9 that is equal to or higher than an optical density value of about 0.2 $OD_{450}$ in a standard ELISA assay.

10. The oligonucleotide decoy of claim 1, wherein the decoy comprises a sequence selected from the group consisting of SEQ ID NOs: 3-35.

11. The oligonucleotide decoy of claim 1, wherein the decoy comprises a sequence that has at least 70% identity with the sequence of SEQ ID NO:28(16.6.5), SEQ ID NO:25(16.6.2), SEQ ID NO:19(17.5), SEQ ID NO:34 (T16.6-T17.5Fu1) or SEQ ID NO:35 (T16.6-T17.5Fu2).

12. A pharmaceutical composition comprising an oligonucleotide decoy of claim 1 or a population thereof and a pharmaceutically acceptable carrier.

13. A kit comprising an oligonucleotide decoy of claim 1 or a population thereof, and optionally an instruction for using said oligonucleotide decoy.

14. A method for modulating nociceptive signaling in a cell comprising administering to the cell an effective amount of an oligonucleotide decoy of claim 1 or a population thereof.

15. A method for treating pain in a subject comprising administering to the subject a therapeutically effective amount of an oligonucleotide decoy of claim 1 or a population thereof.

16. The method of claim 15, wherein the pain is a chronic pain.

17. The method of claim 15, wherein the pain is neuropathic pain.

18. The method of claim 15, wherein the pain is associated with inflammation.

19. The method of claim 15, wherein the pain is associated with the central nervous system or visceral disorder.

* * * * *

UNITED STATES PATENT AND TRADEMARK OFFICE
CERTIFICATE OF CORRECTION

PATENT NO. : 10,287,583 B2
APPLICATION NO. : 15/504191
DATED : May 14, 2019
INVENTOR(S) : Julien Mamet et al.

Page 1 of 1

It is certified that error appears in the above-identified patent and that said Letters Patent is hereby corrected as shown below:

In the Claims

At Column 43, Claim number 1, Line number 40:
"$n_{21}v_{22}n_{23}n_{24}y_{25}m_{26}h_{27}w_{28}b_{29}v_{30}a_{31}$(Formula 1; SEQ ID NO:1);"
Should read:
-- $n_{21}v_{22}n_{23}n_{24}y_{25}m_{26}h_{27}w_{28}b_{29}v_{30}a_{31}w_{32}$ (Formula 1; SEQ ID NO:1); --

Signed and Sealed this
Twenty-third Day of July, 2019

Andrei Iancu
*Director of the United States Patent and Trademark Office*